US009897600B2

(12) United States Patent
Iverson et al.

(10) Patent No.: US 9,897,600 B2
(45) Date of Patent: Feb. 20, 2018

(54) FLOW-THROUGH SENSOR

(71) Applicant: BRIGHAM YOUNG UNIVERSITY, Provo, UT (US)

(72) Inventors: Brian D. Iverson, Provo, UT (US); Kevin M. Marr, Richardson, TX (US)

(73) Assignee: Brigham Young Univerisity, Provo, UT (US)

( * ) Notice: Subject to any disclaimer, the term of this patent is extended or adjusted under 35 U.S.C. 154(b) by 30 days.

(21) Appl. No.: 14/945,234

(22) Filed: Nov. 18, 2015

(65) Prior Publication Data

US 2016/0146805 A1 May 26, 2016

Related U.S. Application Data

(60) Provisional application No. 62/081,330, filed on Nov. 18, 2014.

(51) Int. Cl.
*G01N 21/75* (2006.01)
*G01N 33/543* (2006.01)
*B82Y 15/00* (2011.01)

(52) U.S. Cl.
CPC ........ *G01N 33/54373* (2013.01); *B82Y 15/00* (2013.01)

(58) Field of Classification Search
CPC ................... G01N 33/54373; B82Y 15/00
See application file for complete search history.

(56) References Cited

U.S. PATENT DOCUMENTS

2012/0032366 A1* 2/2012 Ivniski ................ C22C 1/08
264/51

OTHER PUBLICATIONS

Walt, G. D.: "Kinetic evaluation of the viologen-catalyzed carbohydrate oxidation reaction for fuel cell application", Renewable Energy, 2014, 63 (0), 370-375.
Olaussen, J. C. et al.: "Electrochemical glutamate biosensing with nanocube and nanosphere augmented single-walled carbon nanotube networks: A comparative study", Journal of Materials Chemistry, 2011, 21 (30), 11224-11231.
Ohakraborty, S. et al.: "Pt nanoparticle-based highly sensitive platform for the enzyme-free amperometric sensing of H2O2", Biosensors and Bioelectronics, 2009, 24 (11), 3264-3268.
Claussen, J. C. et al.: "Nanostructuring Platinum Nanoparticles on Multilayered Graphene Petal Nanosheets for Electrochemical Biosensing", Advanced Functional Materials, 2012, 22 (16), 3399-3405.
Wang, Z. et al.: "Platinum/graphene functionalized by PDDA as a novel enzyme carrier for hydrogen peroxide biosensor", Analytical Methods, 2013, 5 (2), 483-488.
Xu, F. et al.: "Graphene-Pt nanocomposite for nonenzymatic detection of hydrogen peroxide with enhanced sensitivity," Electrochemistry Communications, 2011, 13 (10), 1131-1134.
Hutchison, D. N. et al.: Carbon Nanotubes as a Framework for High-Aspect-Ratio MEMS Fabrication, Journal of Microelectromechanical Systems, 2010, 19 (1), 75-82.

(Continued)

*Primary Examiner* — Dennis White
(74) *Attorney, Agent, or Firm* — Brake Hughes Bellermann LLP

(57) ABSTRACT

In one general aspect, a flow-through sensor can include a carbon nanotube structure including a parallel array of micro-channels, a catalyst coupled to an inner surface of at least one of the micro-channels, and a functionalizing material disposed within the micro-channels.

20 Claims, 17 Drawing Sheets

(56) References Cited

OTHER PUBLICATIONS

Song, J. et al.: "Carbon-Nanotube-Templated Microfabrication of Porous Silicon-Carbon Materials with Application to chemical Separations", Advanced Functional Materials, 2011, 21 (6), 1132-1139.
Sun, S. et al.: "Synthesis and Characterization of Platinum Nanowire-Carbon Nanotube Heterostructures", Chemistry of Materials, 2007, 19 (26), 6376-6378.
Meng, H. et al.: "Morphology controllable growth of Pt nanoparticles/nanowires on carbon powders and its application as novel electro-catalyst for methanol oxidation", Nanoscale, 2011, 3 (12), 5041-5048.
Tasaltin, C. et al.: "Preparation of flexible VOC sensor based on carbon nanotubes and gold nanoparticles", Sensors and Actuators B: Chemical, 2014, 194 (0), 173-179.
Lalwani, G. et al.: "Fabrication and characterization of three-dimensional macroscopic all-carbon scaffolds", Carbon, 2013, 53 (0), 90-100.
Wang, S. C. et al.: "Enhancement of electrochemical properties of screen-printed carbon electrodes by oxygen plasma treatment", Electrochimica Acta, 2009, 54 (21), 4937-4943.
Yao, Z. et al.: "Highly efficient electrocatalytic performance based on Pt nanoflowers modified reduced graphene oxide/carbon cloth electrode", Journal of Materials Chemistry, 2012, 22 (27), 13707-13713.
Shi, J. et al.: "A comparative study of enzyme immobilization strategies for multi-walled carbon nanotube glucose biosensors", Nanotechnology, 2011, 22 (35), 1-11.
Liu, B. et al.: "Preparation and characterization of size-controlled silver nanoparticles decorated multi-walled carbon nanotubes and their electrocatalytic reduction properties for hydrogen peroxide", Russ J Electrochem, 2014, 50 (5), 476-481.
Claussen, J. C. et al.: "Electrochemical Biosensor of Nanocube-Augmented Carbon Nanotube Networks", ACS Nano, 2009, 3 (1), 37-44.
Soleymani, L. et al.: "Programming the Detection Limits of Biosensors through Controlled Nanostructuring", Nat. Nanotechnol., 2009, 4, 844-848.
Soleymani, L. et al.: "Nanostructuring of Patterned Microelectrodes to Enhance the Sensitivity of Electrochemical Nucleic Acids Detection", Angew. Chem., Int. Ed., 2009, 48, 8457-8460.
Ishida, T. et al.: "Direct deposition of gold nanoparticles onto polymer beads and glucose oxidation with H2O2", J. Colloid Interface Sci., 2008, 323, 105-111.

* cited by examiner

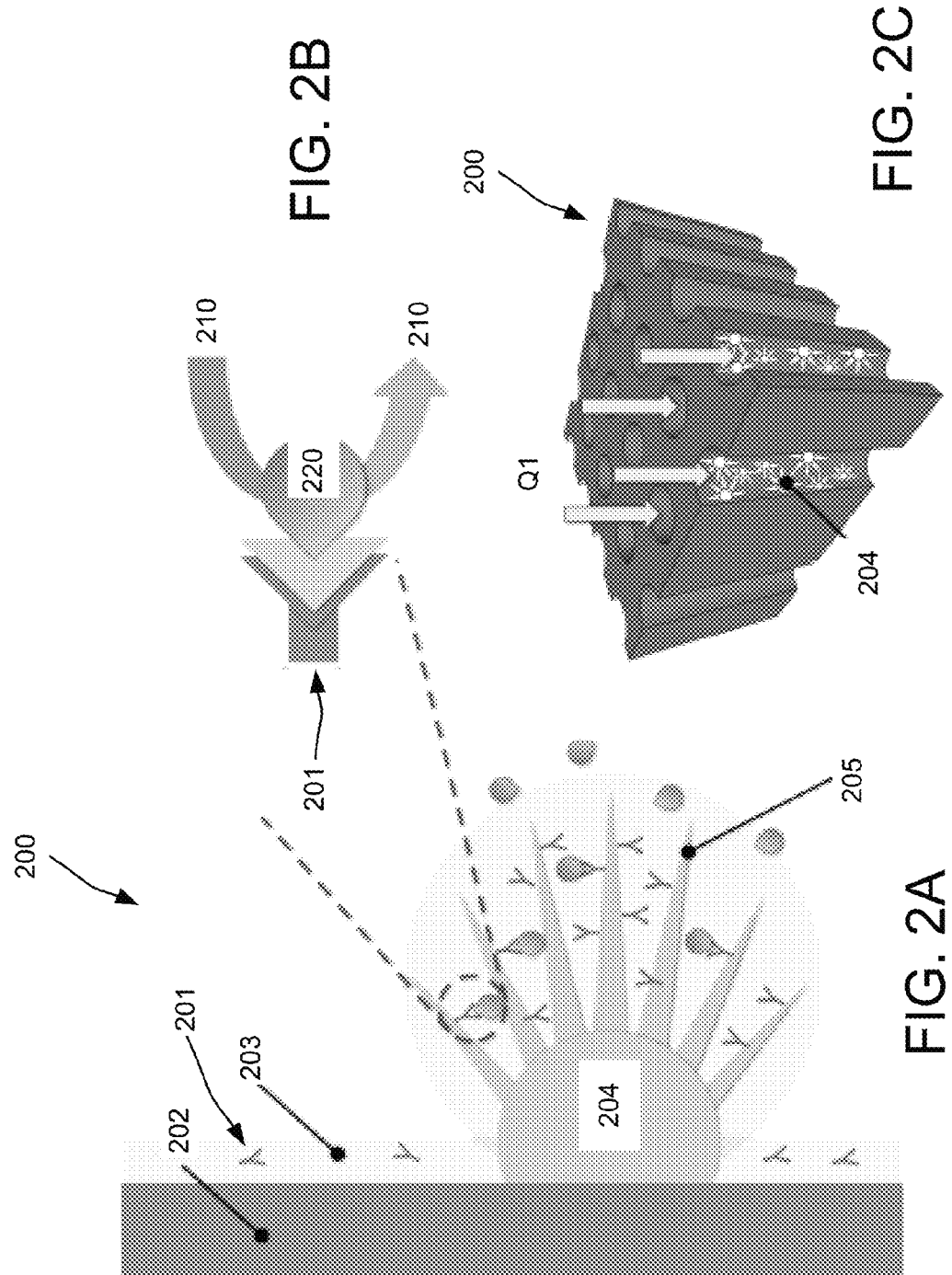

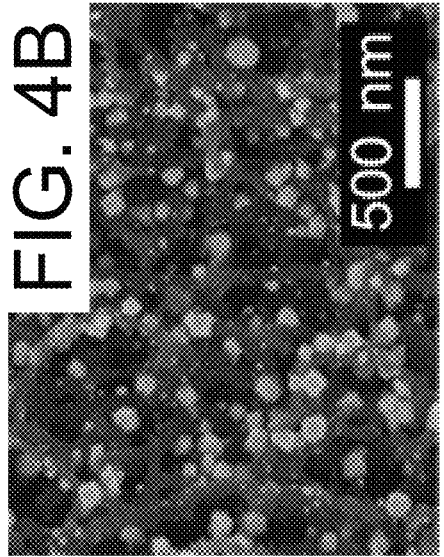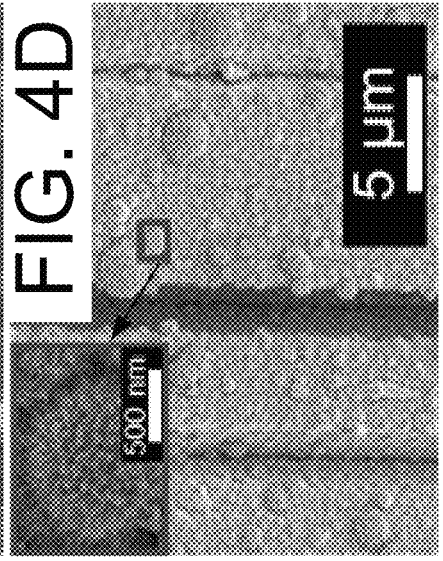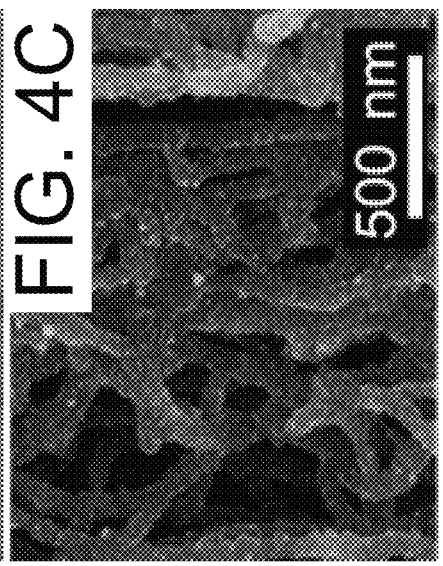

FIG. 6B
FIG. 6C

FLOW-THROUGH SENSOR

RELATED APPLICATION

This application claims priority to and the benefit of U.S. Provisional Patent Application No. 62/081,330, filed Nov. 18, 2014, which is incorporated herein by reference in its entirety.

TECHNICAL FIELD

This description relates to a flow-through sensor.

BACKGROUND

Various techniques and structures have been used to create sensors. However, known sensors such as flat plate sensors can be inefficient and/or ineffective. Thus, a need exists for systems, methods, and apparatus to address the shortfalls of present technology and to provide other new and innovative features.

SUMMARY

In one general aspect, a flow-through sensor can include a carbon nanotube structure including a parallel array of micro-channels, a catalyst coupled to an inner surface of at least one of the micro-channels, and a functionalizing material disposed within the micro-channels.

The details of one or more implementations are set forth in the accompanying drawings and the description below. Other features will be apparent from the description and drawings, and from the claims.

BRIEF DESCRIPTION OF THE DRAWINGS

FIGS. 2A through 2C are diagrams that illustrates a reaction with a flow-through sensor.

FIGS. 4A through 4D are images illustrate resultant nanoparticle morphology and density within carbon nanotube microarray membrane (CNT-MM) structure.

FIG. 6A through 6E are images and graphs related to water droplets on a CNT-MM.

DETAILED DESCRIPTION

Figure 1A:
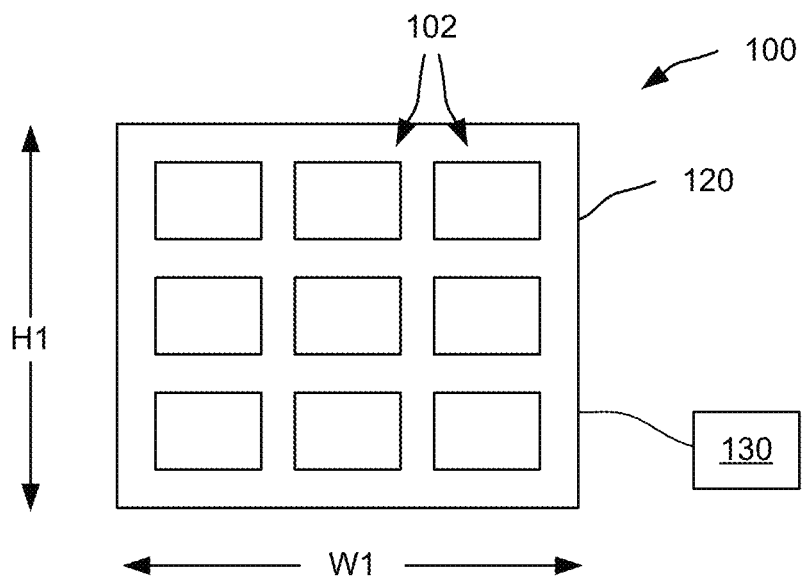
FIG. 1A is a block diagram that illustrates a flow-through sensor according to an implementation.

FIG. 1A is a block diagram that illustrates a flow-through sensor 100 according to an implementation. The flow-through sensor 100 includes several openings, which define lumens 102 (e.g., a pore), through which at least a portion of a fluid (not shown) may flow through the flow-through sensor 100. Specifically, the fluid can flow through element 120, which can be, or can include, a filter or a scaffold.

Figure 1B:
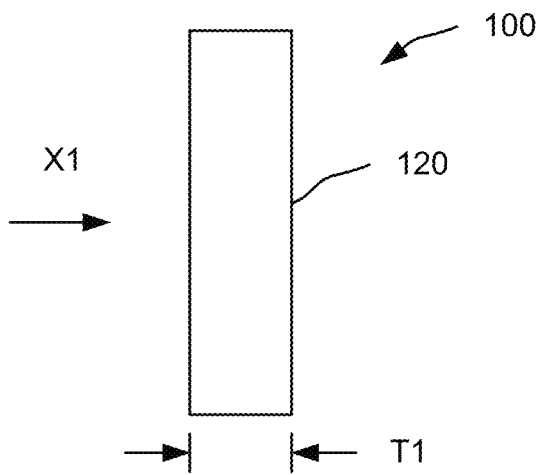
FIG. 1B is a diagram that illustrates a side view of the flow-through sensor shown in FIG. 1A.

As shown, a surface defining at least one or more of the lumens 102 can include a catalytic material (not shown) with which at least a portion of a fluid may react. In other words, one or more catalytic materials can be coupled to (e.g., bound to, deposited on) one or more surfaces defining one or more of the lumens 102. Direction of flow of fluid can be into the page. FIG. 1B is a diagram that illustrates a side view of the flow-through sensor 100. A direction X1 of fluid flow is illustrated in FIG. 1B. In some implementations, a fluid may flow in a different direction (e.g., opposite direction, tangential direction) from direction X1. In FIG. 1B, the element 120, which may include the filter or scaffold, is shown at the outlet side of the flow-through sensor 100. In some embodiments, the element 120, which may include the filter or scaffold may be at the inlet side of the flow-through sensor 100.

In some implementations, the flow-through sensor 100 can include, or can be, a carbon nanotube (CNT) structure. In some implementations, the flow-through sensor 100, or a portion thereof, can be referred to as a microfilter. In some implementations, the flow-through sensor 100 can be a CNT structure that includes, or can be, a carbon nanotube microarray membrane (CNT-MM) structure (e.g., multi-walled carbon nanotube (MWCNT) structure).

In some implementations, a thickness T1 of the flow-through sensor 100 can be less than a height H1 or a width W1 of the flow-through sensor 100 shown in FIG. 1B. In some implementations, the thickness T1 of the flow-through sensor 100 can be greater than or equal to the height H1 or the width W1 of the flow-through sensor 100 shown in FIG. 1B. The thickness T1 can be between a few microns (e.g., 10 µm, 20 µm, 50 µm) and hundreds of microns (e.g., 100 µm, 200 µm, 400 µm), the width W1 and/or height H1 can be approximately between a few microns (e.g., 10 µm, 20 µm, 50 µm) and hundreds of microns (e.g., 100 µm, 200 µm, 400 µm). The openings of the lumens 102 can have an opening size (e.g., a diameter) on the order of less than a micron and a few microns (e.g., 2 µm, 5 µm). Accordingly, the aspect ratio of the lumens 102 can be relatively high.

Said differently, in some implementations, one or more of the micro-channels of a CNT structure included in the flow-through sensor 100 can have a length (or microchannel):width (across the lumen defined by the microchannel) aspect ratio greater than 10:1 (e.g., 40:1, 50:1, 100:1, 200:1, 1,000:1, 10,000:1). In some implementations, one or more micro-channels of the flow-through sensor 100 can have a different aspect ratio. For example, a first micro-channel of the flow-through sensor 100 can have a first aspect ratio and a second micro-channel the flow-through sensor 100 can have a second aspect ratio. As another example, a first micro-channel of a first CNT structure of the flow-through sensor 100 can have a first aspect ratio and a second micro-channel of a second CNT structure of the flow-through sensor 100 can have a second aspect ratio. An example of a CNT structure 300 with a high aspect ratio is illustrated in at least FIG. 3G.

As shown in FIGS. 1A and 1B, a detection mechanism 130 is included in the flow-through sensor 100. The detection mechanism 130 can be configured to detect reactions of a fluid flowing through the flow-through sensor 100 to determine a property of the fluid flowing through the flow-through sensor 100. In some implementations, one or more electrons impacting the flow-through sensor 100 (which can be configured to conduct electricity), or a portion thereof, can be detected by the detection mechanism 130. Specifically, a current generated by electrons impacting the flow-through sensor 100, or a portion thereof, can be detected by the detection mechanism 130.

In some implementations, the lumens 102 of the flow-through sensor 100 can be a two-dimensional array of micro-channels. The lumens 102 can be aligned in parallel with one another within the flow-through sensor 100.

The flow-through sensor 100 can be a miniature or micro sensor that resolves proximity challenges that may be problematic for other known miniature or micro sensors. For example, the flow-through sensor 100 can provide a favorable proximity of analyte to sensing surfaces. Accordingly, the flow-through sensor 100 can be used for relatively low-concentration sensing. For example, in some implementations, the flow-through sensor 100 may be capable of sensing concentrations of approximately 0.05 mM to 50 mM. In some implementations, the flow-through sensor 100 may be capable of sensing concentrations of less than or equal to 0.05 mM, and/or greater than or equal to 50 mM. In addition, the flow-through sensor 100 can provide component proximity and thermal isolation.

As mentioned above, the flow-through sensor 100 can sense molecules (e.g., analytes) suspended in a fluid (liquid or gas). The high surface area to volume ratio structures included in the flow-through sensor 100 can provide intimate contact between the analyte suspension and the sensing surface in a flowing environment. The high surface area to volume ratio and intimate contact between fluid and sensing surface can increase the sensitivity of the flow-through sensor 100.

The flow-through sensor 100 is configured to facilitate intimate contact between molecules in solution (i.e. glucose) and functionalized sensing surfaces thereby facilitating sensing of analytes through boundary layer thinning using novel micro- and nano-structures. In some implementations, the flow-through sensor 100 can be functionalized by a functionalizing material (e.g., a functionalizing material surface, a biorecognition material) included in the flow-through sensor 100. The functionalizing material can be a material that enables detection of a particular material (e.g., an analyte) targeted for detection or a material to aid in a chemical reaction at the surface. In some implementations, an electrical signal can be produced in response to an interaction (e.g., a reaction) of a material targeted for detection and a functionalizing material.

For example, the flow-through sensor 100 can be configured to detect or decompose analytes through high surface area structures that can be placed in a flow path and functionalized to bind analytes in the fluid flowing past the flow-through sensor 100 surface area. Carbon structures and/or novel high aspect ratio carbon nanotube-based filters included in the flow-through sensor 100 can function as the high surface areas scaffold. The carbon structures can have one or more catalytic materials deposited on (or in) them (e.g. platinum) in such a way as to further improve the sensing surface structure and improve catalytic activity. Subsequent biofunctionalization can be used to further increase specificity in sensing target analytes. Since the proximity of analytes and sensing surfaces can be improved by the use of these structures, the functionalized scaffolds could be used to not only detect but also filter out the analyte as it passes through the scaffold. Here the filter (e.g., element 120 shown in FIGS. A and B) can trap particles of a specific makeup through functionalization using a functionalizing material (e.g., a biorecognition material).

In some implementations, the flow-through sensor 100 can be configured to detect glucose levels in bodily fluids. One application of the flow-through sensor 100 can be the monitoring of glucose levels in the body as a mechanism to manage diabetes or provide continuous flow detection during hospitalization. As a body fluid flows through at least a portion of the flow-through sensor 100, glucose may be sensed by flow-through sensor 100 as it binds to a functionalized surface (e.g., glucose oxidase), releases electrons in the process and creates a measurable detection signal in the form of a current.

FIGS. 2A through 2C are diagrams that illustrates a reaction with a flow-through sensor 200. The reaction can be associated with a glucose monitoring process. The diagram illustrates a channel wall 202 of a flow-through sensor 200 (which can be associated with any of the flow-through sensors described herein).

As shown in FIG. 2A, a functionalizing material 201 (which is glucose oxidase in this implementation) is included in (e.g., contained in, coupled to, trapped in, bound to) a layer 203 (which is PEDOT in this implementation). Accordingly, the functionalizing material 201 (and/or the conductive layer) is coupled to (e.g., lines) the channel wall 202 of the flow-through sensor 200. Also, a catalyst 204 (e.g., platinum) is coupled to the channel wall 202. The layer 203 and/or the functionalizing material 201 can be coupled to the catalyst 204. In this implementation, the catalyst 204 has a protrusion(s) 205 (e.g., spindles) which also are coupled to the layer 203 and/or the functionalizing material 201.

In some implementations, the layer 203 can be a conductive layer. The conductive layer can be configured to facilitate transmission of one or more electrical signals produced during one or more interactions (e.g., reactions) occurring within one or more lumens of the flow-through sensor. In some implementations, the thickness of the layer 203 can be relatively thin compared with a thickness of the channel wall 202 (e.g., less than a thickness of the channel wall 202).

In some implementations, the catalyst 204 may not include spindles. In some implementations, the layer 203 and/or the functionalizing material 201 may not be coupled to the catalyst 204. In some implementations, the catalyst 204 may be coupled to the layer 203 and/or the functionalizing material 201 and may not be coupled to the channel wall 202 of the flow-through sensor 200.

FIG. 2B illustrates a reaction that can occur within the flow-through sensor 200. As shown, a target material 220 (e.g., a material targeted for detection, an analyte) interacts with the functionalizing material 201. A reactant 210 can also interact with the target material and/or the functionalizing material 201. A product 212 can be produced in response to the reaction. In the case of glucose monitoring, the target material or analyte can be glucose, the reactant 210 can be $H_2O_2$ and the product 212 can be $O_2$.

In some implementations, a combination of reactions (e.g., a system of reactions, multiple parallel reactions, multiple competing chemical reactions) can occur within the flow-through sensor 200. In some implementations, one or more reactions can occur at (e.g., take place at, be facilitated by) the functionalizing material 201 and/or one or more reactions can occur at (e.g., take place at, be facilitated by) the catalyst 204.

Below are examples of chemical reactions that can be applied using the flow-through sensor described in connection with FIGS. 2A through 2C:

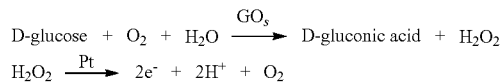

The flow-through sensors (e.g., flow-through sensor 200) described herein can be used to detect glucose in fluids at relatively low concentrations from saliva (between <0.1 mM and <0.2 mM), tears (e.g., between <0.2 mM to <0.4 mM), etc. or in fluids of higher concentrations such as blood (e.g., between <10 mM to <30 mM), as urine (e.g., between <30 mM to >50 mM), etc.

More details regarding $H_2O_2$ decomposition as part of the glucose monitoring is described below. It should be noted that $H_2O_2$ decomposition is presented by way of example only and other types of reactions can be handled by the flow-through sensors described herein. FIG. 2C illustrates a direction Q1 of fluid flow through the flow-through sensor 200 during operation. Also, catalysts 204 are illustrated within the micro-channels of the flow-through sensor 200.

Approximately 25.8 million people in the United States have diabetes, or just over 8% of the total population. It is estimated that another 79 million people have prediabetes or impaired glucose tolerance. This metabolic disorder is a result of, for example, blood glucose concentrations outside of the normal range of 4.4-6.6 mM. As hydrogen peroxide can be formed in the process of glucose detection, the flow-through sensor 100 can also be used to detect or decompose hydrogen peroxide. This may be used by chemical processing plants. Further, in separation technologies where a specific analyte needs to be removed from the fluid, the scaffold could act as a filter for chemical or biological separation.

The flow-through sensor 100 described herein can be more efficient and effective than flow past flat plate structures. The flow-through sensor 100 incorporates flow of fluid through the flow-through sensor 100, which increases proximity of all analytes in the solution to the sensing surface. The flow-through sensor 100 may combine improved proximity with high electron transport scaffolds that have significantly high surface area to volume ratios.

Compared with planar-based devices, the flow-through sensor 100 significantly increases the proximity of an analyte to sensing surfaces. Planar geometries, despite having some surface topography, ultimately suffer from significant separation of the analyte from the sensing surfaces. As a planar sensor detects analytes in the suspension through decomposition, the region near the sensor is slightly depleted of the analyte. Mixing may also counteract this depletion effect. Despite mixing, it is still likely that some of the analyte may never be in close proximity to the sensor. When utilizing flow-through sensor 100 (e.g., a through-flow sensing platform), all (or nearly all) of the analyte passes through the flow-through sensor 100; therefore, the maximum distance between the analyte and sensing surface included in the flow-through sensor 100 will only be as large as the pore radius of the porous filter. As a result, the flow-through sensor 100 is a drastic departure from a planar-based sensing approach utilizing bulk mixing. Further, the flow-through sensor 100 can implement a continuous (or relatively continuous) monitoring approach through continuous flow and has a significantly greater potential for sensing all (or substantially all) analyte molecules present in the suspension. As the transport distance is decreased by improving proximity using through-flow sensing of the flow-through sensor 100, this corresponds to a greater concentration gradient that also would generate a larger mass transfer rate. Given the relatively small diameter through-pores (e.g., lumens 102), the internal flow boundary layer development is significantly restricted and results in short transport distances.

In some implementations, chemical deposition of platinum (Pt) has been shown to result in various nanostructured morphologies. As an example, an advection-enhanced chemical deposition method can be used with the flow-through sensor 100 where forced convection drives fluid through these high aspect ratio channels to improve deposition at locations where transport of chemicals by diffusion alone would be limited. To facilitate nanowire growth along the full channel length, hexachloroplatinic acid, for example, can be pumped through the carbon scaffolds of the flow-through sensor 100 during deposition as opposed to more traditional techniques where the fluid is stagnant or stirred. While stirring may improve deposition on a planar surface or near the edges of porous materials, it does not provide local advection deep in cavities/channels. The resulting Pt nanowire structure and surface coverage enhancement can improve sensitivity of the flow-through sensor 100 by providing more active sensing sites along the flow path. In some implementations, techniques can be used to enable growth of nanowires that protrude from the channel surface of the flow-through sensor 100 into the flow path and act as fin-like structures for improved sensing. In some implementations, physical confinement of transport can be controlled by pore size reduction. As the pore size is reduced, the concentration boundary layer growth can be limited resulting in shorter transport lengths and high mass transport coefficients. Specifically, the mass transport coefficient ($h_m$) can be relatively high for relatively small hydraulic diameters ($D_h$), as $h_m$ is proportional to $1/D_h$.

In some implementations, the element 120 of the flow-through sensor 100, which can be a high surface area to volume ratio, CNT-based catalytic scaffold (filter), can be produced using a fabrication process capable of yielding aligned, high aspect ratio, micro-scale channels. As the flow-through sensor 100 can be used in a tortuous environment, the fabrication process may also provide for adequate structural rigidity. In some implementations, because extended exposure of fuel to catalyst facilitates total fuel decomposition, macro-scale (>0.5 mm) channel lengths may be desirable. Processes for fabricating CNT-based structures may include, for example, screen-printing, electrospraying, alcohol catalytic chemical vapor deposition, self-assembled monolayer linking, thermal crosslinking, and other processes. However, some of these processes may yield insufficient maximum thicknesses or poor feature resolution, or involve the use of toxic chemicals such as, for example, HF and/or chloroform and thorough dispersion.

At least some aspects of the flow-through sensor 100, such as the element 120, can be fabricated using CNT-templated microfabrication. Aspects of the microfabrication process are illustrated in at least FIGS. 3A through 3F. In some implementations, a carbon nanotube-templated microfabrication (CNT-M) process can be used in which lithographically defined iron (Fe) catalyst regions, whereon vertically aligned CNT-MMs are grown in a quartz furnace with ethylene gas ($C_2H_4$) acting as the carbon source (see at least FIGS. 3A through 3D). By a similar chemical vapor deposition (CVD) process, performed at an elevated temperature, the outer walls of the CNT-MMs can be packed (infiltrated) with amorphous carbon or other materials (see at least FIG. 3E). In the extreme case, all, or substantially all voids between neighboring CNT-MMs can be filled with a desired material, thereby forming essentially solid walls patterned according to the existing CNT-MM layout. The variable porosity of the CI-CNT-MM structures, then, can then be controlled by the exposure time of these structures to the infiltration process. FIG. 3F illustrates a fabricated CI-CNT-MM filter with low-porosity sidewall surfaces. The mechanical response of structures fabricated by this method mimic those of the infiltration material.

These capabilities, in conjunction with the precise patterning capabilities of photolithography and the macro-scale growth size of CNT-MMs, allow for the fabrication of a variety of high aspect ratio, nanocomposite materials of varying porosity with enhanced structural integrity In some implementations, the element 120 can be, or can include, a carbon-infiltrated CNT-MM filter (e.g., a carbon-infiltrated CNT-MM).

In some implementations, the CNT-MM filters can be patterned using a close-packed diamond mask (e.g., a close-packed diamond mask with a pore hydraulic diameter of a few microns (e.g., 4.025 μm) and minimum wall thickness of a few microns (e.g., ~2.0 μm)). In some implementations, the prescribed CNT-M parameters may be approximately 800 μm thick, lending to channel aspect ratios of approximately 200:1.

In some implementations, the CNT-MMs can be grown via chemical vapor deposition with pores of a variety of shapes (e.g., diamond shaped pores (nominal diagonal dimensions of, for example, 4.5×9.0 μm)). In some implementations, large surface area and desirable geometry (corners, edges, etc.) catalytic nanoparticles can be coupled to one or more of the pores. In some implementations, an urchin-like, catalytic nanoparticles (e.g., platinum (Pt) nanoparticles, palladium (Pd) nanoparticles, gold (Au) nanoparticles, silver (Ag) nanoparticles, and/or so forth) can be coupled to one or more of the pores via a facile, electroless, chemical deposition process. Accordingly, an CNT-MM including a Pt nanoparticle, for example, can be referred to as a Pt-CNT-MM. The urchin-like shape can include an inner mass (e.g., a sphere-shaped mass or another shaped mass) with spindles or protrusion extending therefrom. In some implementations, a CAT-CNT-MM (where CAT represents a catalytic material) can a have a robust, high catalytic ability with a desirable effective activation energy (e.g., an activation energy of 26.96 kJ mol$^{-1}$)

Carbon nanotube (CNT)-templated microfabrication, which can be included in the flow-through sensor 100, is an approach to constructing high aspect ratio structures that capitalizes on the very large length to diameter ratios present for carbon nanotubes. For modest growth lengths of, for example, 1 mm and a nominal spacing of, for example, 100 nm between carbon nanotubes, aspect ratios of, for example, 10-10,000 are achievable for vertically aligned growth. When combined with lithographically defined growth, almost any aspect ratio in this range can be realized. This range is significantly better than typical etching techniques for high aspect ratio structures such as Deep Reactive Ion Etching (DRIE) and offers distinct advantages over Lithography, Electroplating, and Molding (LIGA) in cost, time, and scalability. Using patterned CNTs as a scaffold, additional materials can be coated on or infiltrated into the forest, making these structures rigid and reinforced. The conditions and duration of an infiltration procedure can be controlled to result in highly dense or highly porous regions. Therefore two-tier, porous materials can be constructed with CNT-templated microfabrication; larger (micron-scale) spacings controlled by lithography and smaller (nanometer-scale) spacings controlled by carbon nanotube forest density and subsequent infiltration. Multi-walled carbon nanotube (CNT-MM) fabricated by this method thereby provide a versatile microstructure for reagent-based burst-propulsion. Thus, this distinct CNT-templated microfabrication process enables the growth of aligned, high aspect ratio CNT microchannel membranes—a three-dimensional microstructure that may not be formed from conventional, stand-alone CNT fabrication techniques such as screen-printing, electrospraying, alcohol catalytic chemical vapor deposition, plasma-enhanced chemical vapor deposition, self-assembled monolayer linking, and thermal crosslinking.

CNT-MM structures, which can be included in the flow-through sensor 100, can be functionalized using electroless deposition of a catalyst such as Pt onto CNTs to provide highly catalytic microstructures for burst-propulsion applications. For example, deposition by the reduction of chloroplatinic acid can be one-step process offering several advantages. Most notably is that the morphology and density of, for example, Pt nanoparticles on carbon structures is controllable. Similar depositions can be performed on highly ordered 3D graphene. This technique can provide effective electrocatalytic functionalization for scalable substructures. Furthermore, Pt deposited in this fashion on nanocellulose can be highly durable. Based on this, electroless deposition of Pt nanoparticles by the reduction of chloroplatinic acid can provide a controllable, scalable, and mechanically robust catalytic structure for the aggressive decomposition of $H_2O_2$ at relatively high concentrations (e.g., 50% w/w).

Following deposition, CAT-CNT-MMs, which can be included in the flow-through sensor 100, can be inspected and characterized using both scanning electron microscopy (SEM) and transmission electron microscopy (TEM). In some implementations, for example, Pt-CNT-MMs can have continuous coverage of Pt on the CNT micro-channels. These catalytic structures can have hydrophobicity (from water contact angle analysis), electroactive specific surface area (from cyclic voltammetry (CV) experiments), surface area calculated (from Brunauer-Emmett-Teller (BET) analysis on nitrogen adsorption experiments), as well as effective activation energy (from $H_2O_2$ decomposition profiles).

The microfabrication process can include exploiting lithographically defined metal (e.g., iron (Fe)) catalyst regions, whereon vertically aligned CNT forests can be, for example, grown in a quartz tube furnace with, for example, ethylene gas ($C_2H_4$ at 750° C.) acting as the carbon feedstock gas (shown in at least FIGS. 3A through 3D). By a similar chemical vapor deposition (CVD) process, for example, performed at an elevated temperature (900° C.), these CNT forests can be infiltrated with a mixture of graphitic and amorphous carbon (or other materials) to coat the outer walls of the CNTs (shown in FIG. 3E). In some cases, all (or substantially all) void space between CNTs can be filled with a desired material, thereby forming solid walls patterned according to the existing CNT layout during growth. The variable porosity of the CNT structures is controlled in part by the exposure time of these structures to the infiltration process.

FIG. 3F illustrates a representative carbon-infiltrated CNT-MM (CNT is herein taken to mean carbon-infiltrated CNT) with low-porosity sidewall surfaces. The precise patterning capabilities of photolithography and the macro-scale growth size of CNTs, in conjunction with the added structural versatility afforded by CNT-templated microfabrication, allows for the creation of a variety of high aspect ratio, nanocomposite materials of varying porosity/composition with enhanced structural integrity.

Figure 3A:
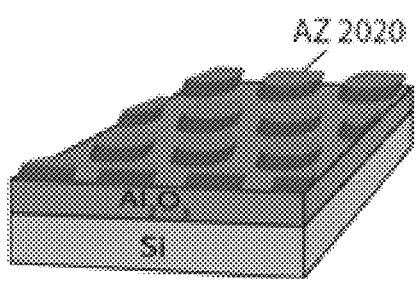
FIGS. 3A through 3G illustrate aspects of a flow-through sensor microfabrication process.
Figure 3B:
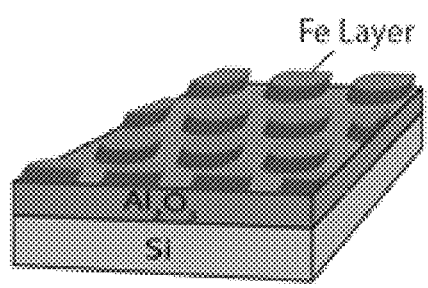
Figure 3C:
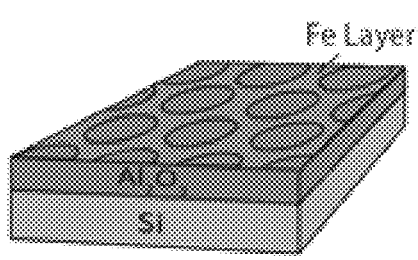
Figure 3D:
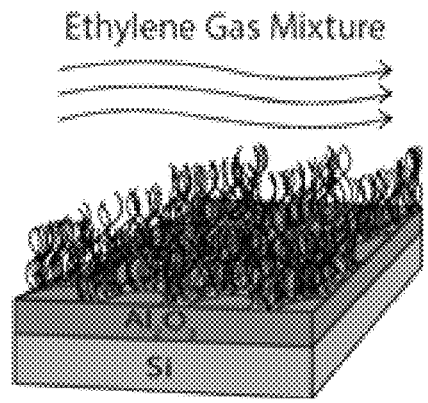
Figure 3E:
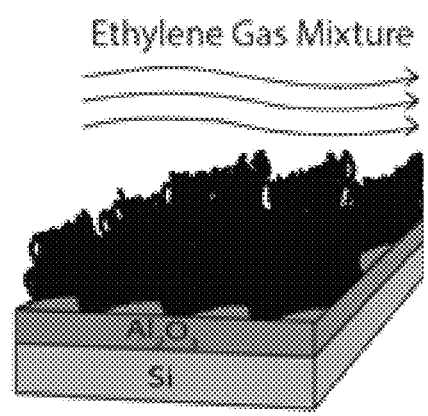
Figure 3F:
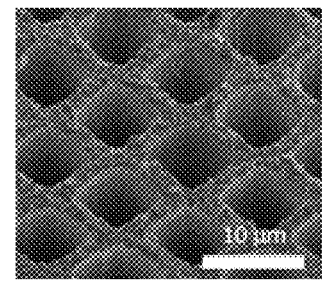

In summary, FIG. 3A illustrates photoresist being patterned onto a silicon (Si) wafer coated with alumina ($Al_2O_3$). FIG. 3B illustrates thermal evaporation of iron (Fe) for CNT growth. FIG. 3C illustrates a resultant Fe pattern after solvent lift-off process to obtain hydraulic diameters of a few microns (e.g., 4.025 μm). FIG. 3D illustrates CVD growth of high-aspect ratio CNT-MMs (e.g., ~600 μm height) with an ethylene gas mixture as the carbon feedstock gas. FIG. 3E illustrates carbon-infiltration of CNT-MM. FIG. 3F illustrates an SEM image of resultant CNT-MM structure. Although a particular process is described, in some implementations, the reactants, process steps, and/or so forth can be modified.

In some implementations, the CNT-MMs included in the flow-through sensor 100 can be patterned using a close-packed, diamond-shaped channel mask. In some implementations, the CNT-MMs can have a different profile shape or pattern (e.g., a circular pattern, a hexagonal pattern, a square or rectangular pattern, an irregular or regular pattern of different shapes or profiles) (when viewed along a direction of the microchannels). In some implementations, a hydraulic diameter of greater than a few microns, or less than a few microns can be defined within the CNT-MMs. In some implementations, CNT-MMs with a wall thickness (e.g., minimum wall thickness) of a few microns or less can be defined (e.g., ~2.0 μm). In some implementations, additional CNT-templated microfabrication parameters can be used to define CNT-MMs with a variety of dimensions (e.g., approximately 600 μm thick with channel aspect ratios of 150:1).

In some implementations, reactive ion etching (ME) can be used to remove the carbon floor layer formed at the base of the CNT-MM against the substrate during the CVD infiltration process. In some implementations, the ME process can also function to enhance subsequent metallic deposition, therefore, the face opposite the carbon floor layer can also be etched. In some implementations, prior to platinum deposition, reactive ion etching (RIE) may be used to remove the carbon floor layer formed at the base of the filter (e.g., element 120) against the substrate during the CVD growth process. In addition to exposing the microchannel pores, the ME process may enhance carbon affinity to subsequent metallic depositions as well as bolster electrocatalytic performance.

In some implementations, nanostructured morphologies of a catalyst (e.g., Pt catalyst) can be tuned and subsequently exploited to enhance electrocatalytic performance of the flow-through sensor 100. Specifically, needle-like or urchin-like structures display favorable electrocatalytic activity because of their large surface area and desirable geometry (corners, edges, etc.). As a specific example, this morphology is desirable for $H_2O_2$ decomposition, and can be achieved by chemically depositing Pt under conditions of relatively low solution pH ($\leq 2.5$) and relatively high Pt loading concentration ($\geq 20\%$ w/w Pt—C) resulting in growth of relatively dense Pt nanowires (approx. 10-30 nm in length and 3-4 nm in diameter) on non-porous, singular carbon spheres, carbon nanotubes, and cellulose paper as well as three-dimensional graphene.

Specifically, highly catalytic urchin-like Pt can be deposited as nanoparticles onto the CNT-MMs. In some implementations, the Pt can be deposited deep within the CNT microchannels. Electroless deposition can be performed on a per-mass basis and can involve CNT-MM submersion in a static solution of relatively low pH (<1.5) and high Pt molarity ($H_2PtCl_6 \cdot (H_2O)_6$ at ~10 mM) for each deposition. Dense coverage of urchin-like Pt nanoparticles is produced as the reduction time of the Pt precursor is increased. This is realized when there is an abundance of $H^+$ ions in solution (i.e., low pH). Given that no base additives may employed in some implementations, solution pH can be inversely related to Pt molarity. Thus, for a given volume of solution, the desired Pt nanoparticle morphology and density can be obtained by increasing the Pt—C loading of the solution (25-30% w/w Pt—C) and maintaining a low solution pH (<1.5).

Figure 3G:
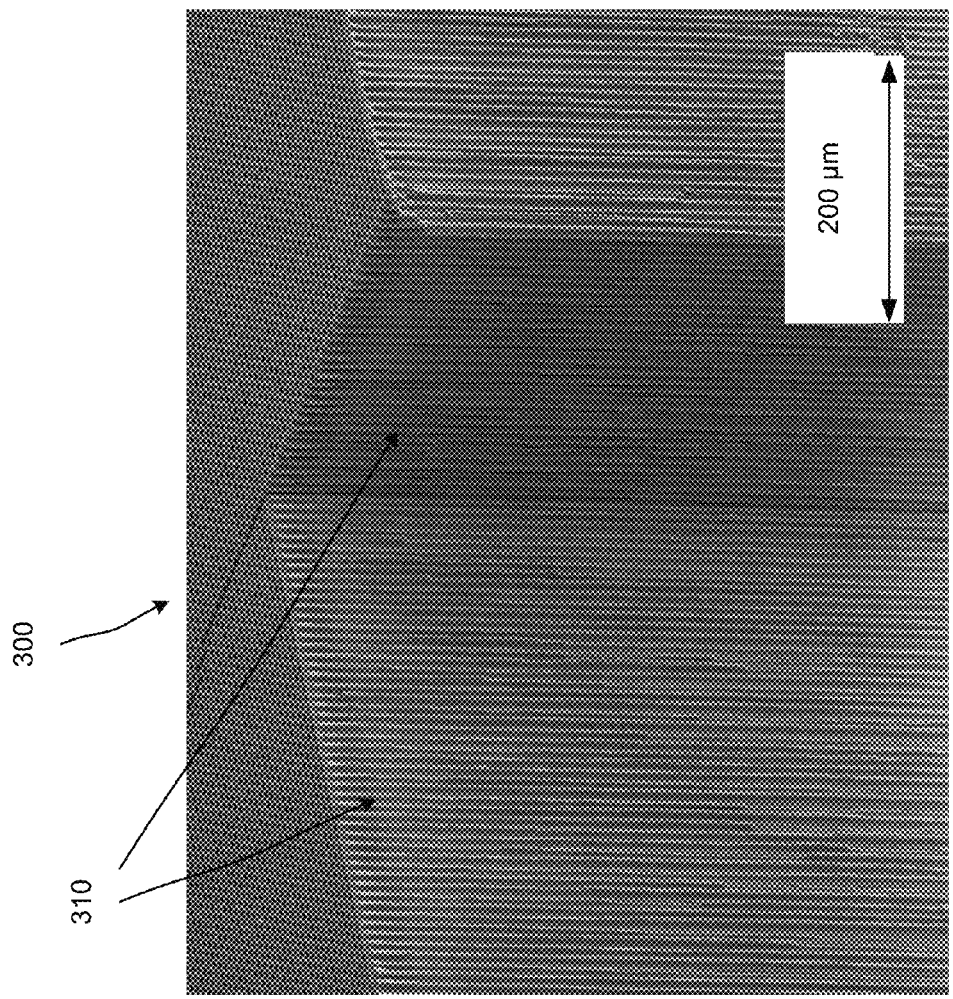

FIG. 3G illustrates a CNT structure 300 with a high aspect ratio. As shown in FIG. 3G, the CNT structure 300 includes micro-channels 310 defining relatively long lumens compared with the widths of openings at the ends of the micro-channels 310.

FIGS. 4A through 4D are images via SEM that illustrate resultant Pt nanoparticle morphology and density within Pt-CNT-MMs (which can be used in a flow-through sensor such as flow-through sensor 100 shown in FIG. 1). FIG. 4A illustrates that the entry region sidewalls of a Pt-CNT-MM are uniformly covered with dense urchin-like Pt clusters, a Pt morphology that resembles those produced in, for example, 60% w/w Pt—C solution and 2.5 pH loadings. Around these entry regions, Pt clusters are observed to protrude from the sidewall into the microchannel by as much as, for example, 400 nm. The apparent roughness that these clusters, and their urchin-like structure, add to the microchannels can facilitate additional fuel/catalyst interaction.

FIGS. 4B and 4C are images at successively longer distances (approximately 25 μm and 280 μm, respectively) into the CNT-MM microchannel. In some implementations, FIG. 4C can be an image at a center of a microchannel depth. FIGS. 4B and 4C reveal a uniform spread of Pt catalyst ranging in maximum centripetal protrusion lengths of approximately 120 nm and 13 nm, respectively. Hence, the size of urchin-like Pt nanowires near the midpoint of each microchannel can be considerably smaller than their entry-region counterparts. Nevertheless, evidence of Pt coverage in the axial center (e.g., center portion) of the channel indicates that static Pt deposition is indeed configured to reach even the most inward portions of the CNT microchannels. Furthermore, SEM imaging in FIG. 4D of a peripheral region of the Pt-CNT-MMs shows the high affinity of Pt precursor to the $O_2$ etched CNT-MM structure. Comparison of the lightly coated inner regions of the Pt-CNT-MM against the densely coated peripheral regions suggest that exposure to the bulk Pt solution enhances Pt coverage, and thus the deposition process is likely diffusion-limited near the axial center of the channel. In some implementations, improved coverage of the deposition process can be achieved in non-quiescent environments such as flowing deposition conditions. FIG. 4D is an image of total coverage along periphery of Pt-CNT-MM with inset showing the urchin-like morphology and arrangement of the deposited Pt. Although FIGS. 4A through 4D are focused on Pt catalysts, similar characteristics can be obtained for other types of catalysts.

Figure 5A:
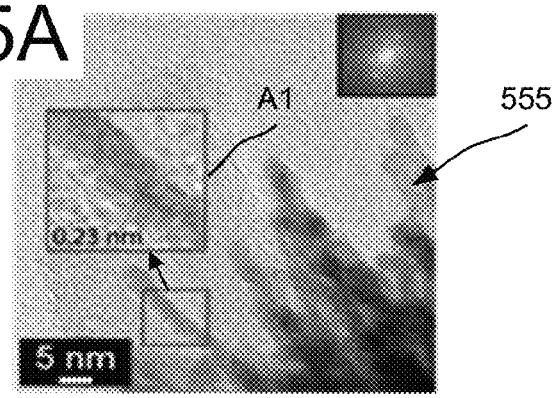
FIGS. 5A through 5D are images used to confirm the deposition of nanoparticles onto CNTs
Figure 5B:
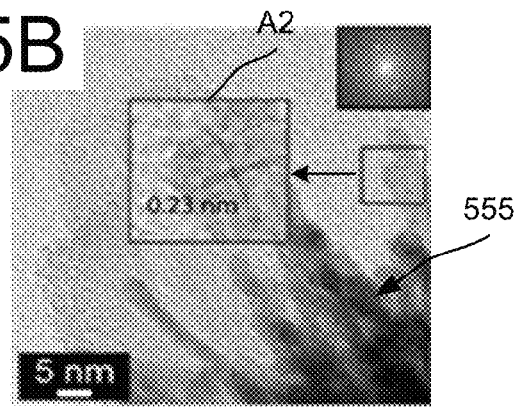
Figure 5C:
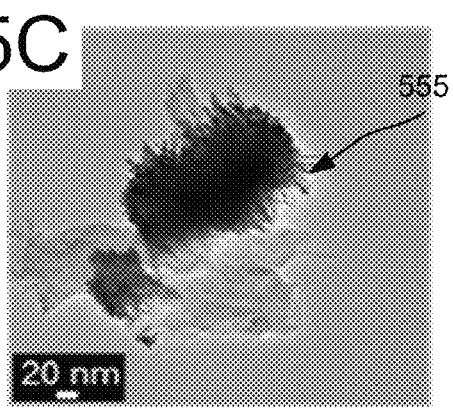
Figure 5D:
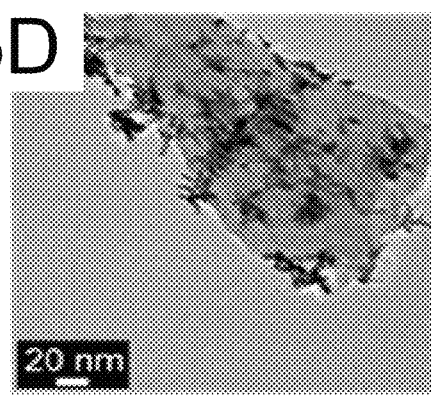

FIGS. 5A through 5D are high-resolution TEM images that illustrate the deposition of Pt nanoparticles onto CNTs (which can be used in a flow-through sensor such as flow-through sensor 100 shown in FIG. 1), as well as further characterization of the dimensions of the Pt nanowires 555. FIGS. 5A and 5B illustrate a d-spacing between (111) planes of 0.23 nm within the Pt-CNT-MM by TEM, confirming that the deposited nanoparticles are Pt. Specifically FIG. 5A illustrates a TEM image showing lattice spacing of a synthesized Pt nanowire 555 with Fast Fourier Transform (FFT) inset A1. FIG. 5B illustrates the same TEM image as in FIG. 5A showing the lattice spacing of the Pt nanowire 555 on the same cluster but having different crystal plane orientation with FFT inset A2. TEM analysis further confirms that the larger Pt urchins have nanowires 555 with lengths of up to 30 nm. Morphologies of this type, as illustrated in FIG. 5C, dominate the entry regions of the Pt-CNT-MM microchannels whereas smaller clusters, as illustrated in FIG. 5D, fill the central interior for deposition in quiescent conditions. It is also shown that urchin-like Pt nanowires 555 in the central interior are half this maximum length, or approximately 15 nm. Pt nanowire 555 diameters measured, however, can coincide with the 3 nm dimension typically observed here. While average Pt nanowire 555 dimensions (length and diameter) are consistent between clusters at comparable regions along (e.g., axially along) the Pt-CNT-MM channels, the orientation of their (111) planes can vary drastically, in some implementations, between nanowires 555, regardless of region and cluster. FIG. 5C illustrates a fragment having dense Pt cluster coverage and large growth size, similar to the entrance region of Pt-CNT-MM microchannels. FIG. 5D illustrates a fragment having less dense urchin-like Pt cluster coverage and smaller growth size, similar to the central interior of Pt-CNT-MM.

Due to their high surface energy and micro/nanoscale surface roughness, CNT structures that can be included in a flow-through sensor 100 such as shown in FIGS. 1A and 1B can be natively hydrophobic. Introducing capillary action via hydrophilic enhancement of CNTs facilitates intimate contact between fuel (an aqueous reagent) and catalyst, thereby lending to improved fuel decomposition rates. In order to provide hydrophilic enhancement without jeopardizing the structural integrity of the Pt-CNT-MM, a controllable hydrophilic enhancement scheme can be included, suitable to CNT structures.

In some implementations, hydrophobic disposition of CNT substrates can be altered by ultraviolet assisted ozone treatment, RIE, chemical oxidation and subsequent functionalization, chemical etching, and by patterning the CNTs to form hydrophobic topologies. In some implementations, $O_2$ RIE can be used because it allows for a controllable means of modifying the CNT surfaces to be hydrophilic. Accordingly, in some implementations, each CNT-MM included in the flow-through sensor 100 can be exposed to a brief $O_2$ etch after growth to improve the penetration of aqueous solution into the CNT-MM pores during Pt deposition.

Figure 6A:
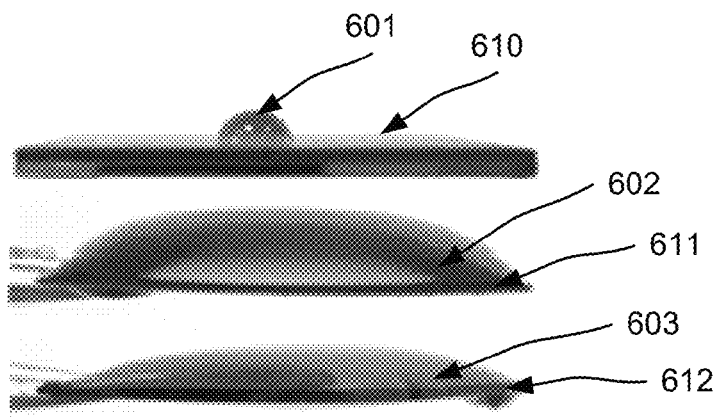

In some implementations, the hydrophobic nature of the CNT-MMs can be observed during each stage of the fabrication process. FIG. 6A through 6C illustrate images of ultrapure water droplet(s) on a CNT-MM at various stages of fabrication (all images taken at same magnification) according to an example implementation.

In some implementations, ultrapure water droplets (10 μL) can be dispersed onto separate regions across the surface of a CNT-MM flow-through sensor before $O_2$ etching. In some implementations, the water droplets may not appear to wet the CNT-MM channels at any appreciable rate indicating that the surface appeared to be hydrophobic as shown in FIG. 6A. This observation can be confirmed as the wetting angle of each droplet can be measured using, for example, a Ramé-Hart precision contact angle goniometer, and can be found to have an average value of 110.6±2.1°. This angle can be indicative of a hydrophobic surface, but is lower than the reported water contact angles for CNTs given in related studies. This discrepancy can be caused by the smooth graphitic/amorphous carbon coating on the outer walls and caps of the CNTs.

Specifically, FIG. 6A illustrates a water droplet 601 on a CNT-MM 610 (which can be used in, or as, a flow-through sensor) before $O_2$ RIE, showing hydrophobic nature of CNTs. FIG. 6B illustrates a water droplet 602 wicking through and dispensing on top of an $O_2$ RIE etched CNT-MM 611 (which can be used in, or as, a flow-through sensor), showing a hydrophilic nature. FIG. 6C illustrates a water droplet 603 wicking through and dispensing on top of a Pt-CNT-MM 612 (which can be used in, or as, a flow-through sensor), also exhibiting hydrophilic response.

Figure 6D:
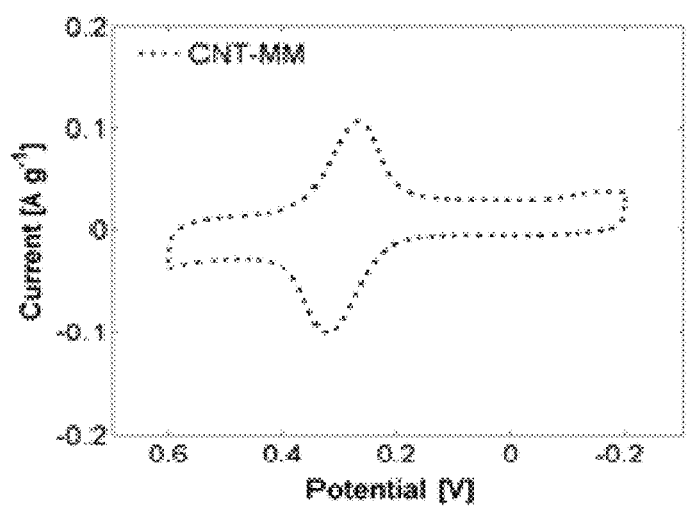

FIG. 6D illustrates a current-voltage characterization of CNT-MM flow-through sensor within ferricyanide mediator solution (4 mM $Fe(CN)_6^{3-}$ and 1 M $KNO_3$). Representative cyclic voltammogram (current normalized by flow-through sensor mass) for a CNT-MM flow-through sensor. FIG. 6D illustrates a plot of the magnitude of the normalized anodic peak current vs. the square root of the scan rate for a CNT-MM flow-through sensor, indicating that the transport of ferricyanide to the CNT-MM surface is a diffusion-controlled process.

In some implementations, post $O_2$ etched CNT-MM flow-through sensors can have hydrophilic behavior as water can spread along the top surface of the membrane and then wick through to the bottom surface of the membrane as shown in FIG. 6B. Similar hydrophilic behavior can be exhibited by the Pt-CNT-MM as shown in FIG. 6C. In some implementations, if the channel sidewalls can be hydrophobic at these stages, aqueous solution would not fill a small channel of this diameter due to the inability to overcome the Laplace pressure. In some implementations, as a result of the spreading and capillary action, no contact angles are reported for either the $O_2$ etched CNT-MM flow-through sensors or Pt-CNT-MM flow-through sensors. In some implementations, these wetting observations support the additional characterization by electrochemical means (which are aqueous-based), as well as subsequent use in propulsion generation where aqueous-based fuel (i.e., $H_2O_2$) effectively penetrate the pores of the Pt-CNT-MM for catalysis.

In some implementations, current-voltage analysis can be employed to quantify the electroactive surface area for CNT-MMs fabricated under prescribed conditions. In some implementations, CV tests can be conducted for CNT-MM flow-through sensors acting as the working electrode, a Ag/AgCl electrode acting as the reference electrode and a coiled Pt wire as the counter electrode. In some implementations, initial tests can be ere performed using a ferricyanide solution acting as mediator.

In some implementations, electroactive surface areas (EASAs) can be calculated using the Randles-Sevcik Equation (Equation 1), where $i_p$ is the peak redox current A, n is the number of electrons transferred per redox reaction, A is the EASA cm$^2$, D is the mediator diffusion coefficient ($6.7 \times 10^{-6}$ cm$^2$ s$^{-1}$ for a ferricyanide solution of 4 mM Fe(CN)$_6^{3-}$ and 1 M KNO$_3$), c is the solution concentration mol cm$^{-3}$, and v is the potential scan rate V s$^{-1}$. $^{60}$CVs obtained with a potential scan that can be cycled between −0.2 and 0.6 V versus the Ag/AgCl reference electrode with a scan rate of 10 mV s$^{-1}$ (See FIG. 6D).

$$i_p = 2.686 \times 10^5 n^{3/2} AcD^{1/2} v^{1/2} \quad (1)$$

In some implementations, to allow for comparison between CNT-MMs of any dimension as well as account for variations in growth across the CNT-MM surface, CV data can be normalized according to flow-through sensor mass. Hence, EASA calculations can be used to determine the electroactive specific surface area (SSA, EASA per unit mass) for each flow-through sensor. In some implementations, CNT-MM can have an average SSA of 293±28 cm$^2$ g$^{-1}$.

Figure 6E:
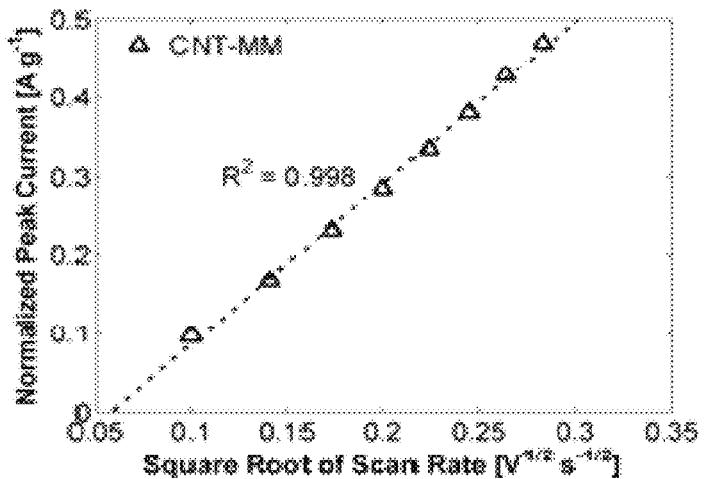

In some implementations, a linear relationship can exist between the magnitude of the normalized anodic peak current and the square root of the scan rate for the CNT-MM flow-through sensor within the ferricyanide mediator solution as shown in Error! Reference source not found. FIG. 6E. This linear correlation ($R^2$ values>0.99) suggests that the redox reaction of ferricyanide at the surface is a diffusion-controlled process for CV in a static environment.

CNT-MM flow-through sensors can exhibit a type II nitrogen adsorption isotherm indicative of a macroporous material, with an average calculated BET surface area of, for example, 61 m$^2$ g$^{-1}$ and a pore volume of 0.118 cm$^3$ g$^{-1}$. Table 1 shows the average calculated BET surface area for CNT-MM flow-through sensors with comparison to similar structures. Most notably, the BET surface area for the CNT-MMs is approximately half that of pristine CNTs. This is likely attributable to the carbon-infiltration step of the CNT-MM fabrication process, which not only contributes additional mass throughout the structure, but may also cause a reduction in surface area by joining adjacent CNTs. However, the infiltration procedure allows for controllable porosity (mass/surface area) and improved structural integrity.

TABLE 1

Comparative BET surface area values.

| Structure | BET Surface Area (m$^2$ g$^{-1}$) |
|---|---|
| Pristine CNTs | 131 |
| Polycarbonate Monolith | 69 |
| CNT-MM | 61 |
| Polyacrylonitrile Membrane | 39 |
| Zirconia Microtube | 23 |

The effectiveness and durability of catalysts for $H_2O_2$ decomposition within the flow-through sensor 100, for example, can be dependent upon multiple factors including material composition, surface area, and reaction temperature. Namely, catalytic performance can be an ability to reduce the activation energy required for a given chemical reaction. A variety of catalysts can be used for lowering the activation energy associated with $H_2O_2$ decomposition including metal catalysts (e.g., Pt, Pd, Au and Ag) as well as metal oxide catalysts (e.g., MnO$_2$, Fe$_2$O$_3$, K$_2$Cr$_2$O$_7$). In some implementations, although highly effective at lowering the activation energy of $H_2O_2$ decomposition, metal oxide catalysts can be consumed during $H_2O_2$ decomposition. Accordingly, in some implementations, metal catalysts can be used in the flow-through sensor 100. In some implementations, the effectiveness of metal catalysts for $H_2O_2$ decomposition can be proportional to the exposed catalyst surface area. In some implementations, in the case of Pt catalysts, more exposed metal correlates to more free catalytic sites available for Pt—(OH) and Pt—(H) binding—two reactions that are involved in the eight kinetic steps in $H_2O_2$ decomposition with Pt metal catalysts. Furthermore, in some implementations, the reaction rate for the decomposition of $H_2O_2$ can tend to dramatically increase as the temperature of the exothermic reaction increases. In some implementations, this phenomenon can be due to the auto decomposition of $H_2O_2$ at elevated temperatures and to the fact that oxygen solubility remains low even at higher temperatures. Hence the reaction rates of $H_2O_2$ decomposition can tend to increase due to the conflation of both increased surface area and reaction temperature in some implementations.

In some implementations, transport processes may also alter the performance of the Pt-CNT-MM catalysts within the flow-through sensor 100, including the following: transport of reactants from the main fuel stream to the Pt-CNT-MM surface; transport of reactants within the CNT microchannels to the Pt metal surface; adsorption/desorption of reactants/products at the Pt metal surface; transport of desorbed products from the Pt metal through the CNT microchannels; and transport of desorbed products from within the CNT microchannels to the main stream of fluid. Consequently, the activation energy can change according to the rate of flow introduced into the reaction chamber. Therefore, an effective activation energy of the Pt-CNT-MM as measured within a convective fuel flow field can mimic, in part, the convective flow field that would be experienced in an actual MUV reaction chamber. In some implementations, the impact of convection on activation energy may not be considered and often the conditions of fluid stirring are not provided. In some implementations, the activation energy under flowing conditions can be equivalent to the effective activation energy, though specific to the conditions of the flow field.

Referring back to FIG. 1, implementations of the various aspects described herein (e.g., such as those associated with the detection mechanism 130) may be implemented in digital electronic circuitry, or in computer hardware, firmware, software, or in combinations of them. Portions of methods also may be performed by, and an apparatus may be implemented as, special purpose logic circuitry, e.g., an FPGA (field programmable gate array) or an ASIC (application-specific integrated circuit).

In some implementations, the detection mechanism 130 can include a processor such as a microcontroller. In some implementations, the detection mechanism 130 can include one or more wireless devices configured to transmit and/or send wireless communications. In some implementations, the detection mechanism 130 can include an electronic storage component such as a memory.

Some portions of the detection mechanism 130 may be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. Components may be interconnected by any form or medium of digital data communication, e.g., a communication network. Examples of communication networks include a local area network (LAN) and a wide area network (WAN), e.g., the Internet.

Figure 7:
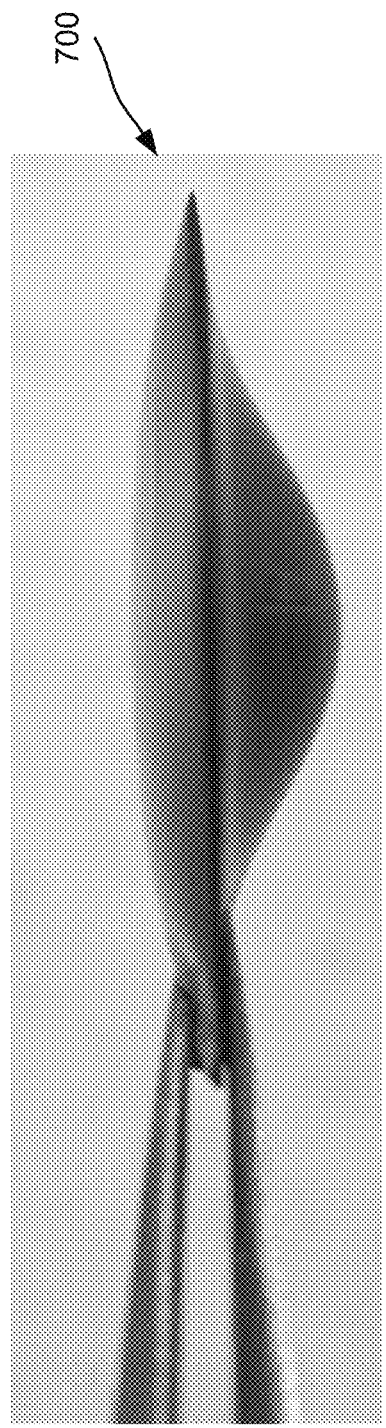
FIG. 7 illustrates a liquid drawn through the flow-through sensor and element 120 including a filter and/or scaffold by a capillary flow action.

FIG. 7 illustrates a liquid drawn through the flow-through sensor 700 and element including a filter and/or scaffold by a capillary flow action. Due to the relatively small feature size of the micro channels fabricated using a carbon nanotube scaffold, the filters can also be used to pump liquid into the pores using capillary action. In this manner, the flow may be driven passively into or through the pores without the use of an external pumping mechanism. Rather, fluid solutions containing analytes of interest could be pumped through the flow-through sensor 700 by capillary pressure. These analytes may again be brought into close contact with sensing surfaces due to the small hydraulic diameter.

Figure 8A:
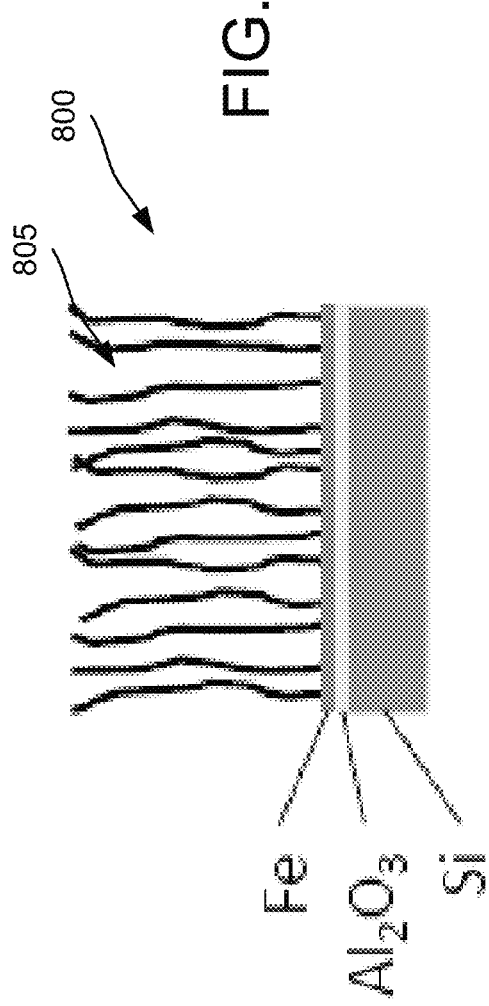
FIG. 8A is a diagram that illustrate templated manufacturing in an overlaid fashion in a flow-through sensor.

FIG. 8A is a diagram that illustrate templated manufacturing in an overlaid fashion in a flow-through sensor 800. The patterned CNT growth in the flow-through sensor 800 illustrates relatively tall features. Infiltration of materials (described in connection with FIG. 8B) can be used to control porosity and/or density of microchannels 805 within the flow-through sensor 800. In some implementations, the structure (or portions thereof) can be electrically conductive or insulating.

Figure 8B:
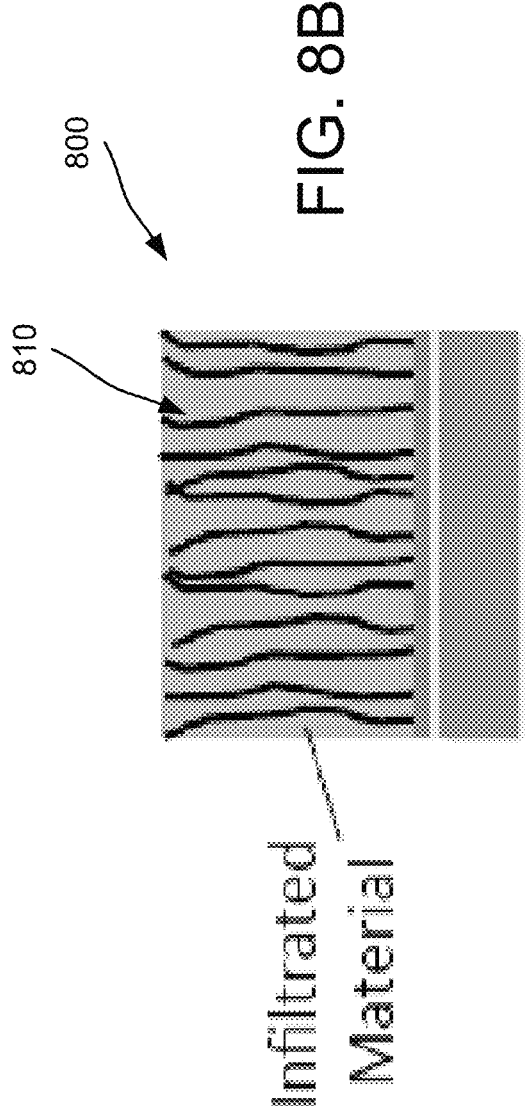
FIG. 8B is a diagram that illustrates an infiltration material included in the flow-through sensor shown in FIG. 8A.

FIG. 8B is a diagram that illustrates an infiltration material 810 included in the flow-through sensor 800 shown in FIG. 8A. The infiltration material 810 can be included in the flow-through sensor 800 using a variety of methods including chemical vapor deposition (CVD) (e.g., low pressure CVD), electrochemically, chemical deposition, and/or so forth. The infiltrated materials 810 can include silicon or silicon dioxide, a metal (e.g., nickel (Ni), platinum (Pt)), a carbon-based material (e.g., amorphous carbon), and/or so forth.

As noted above, the electroactive surface area (EASA) for a flow-through sensor can be determined via cyclic voltammetry (CV). EASAs can be calculated using, for example, a Randles-Sevcik equation.

Figure 9:
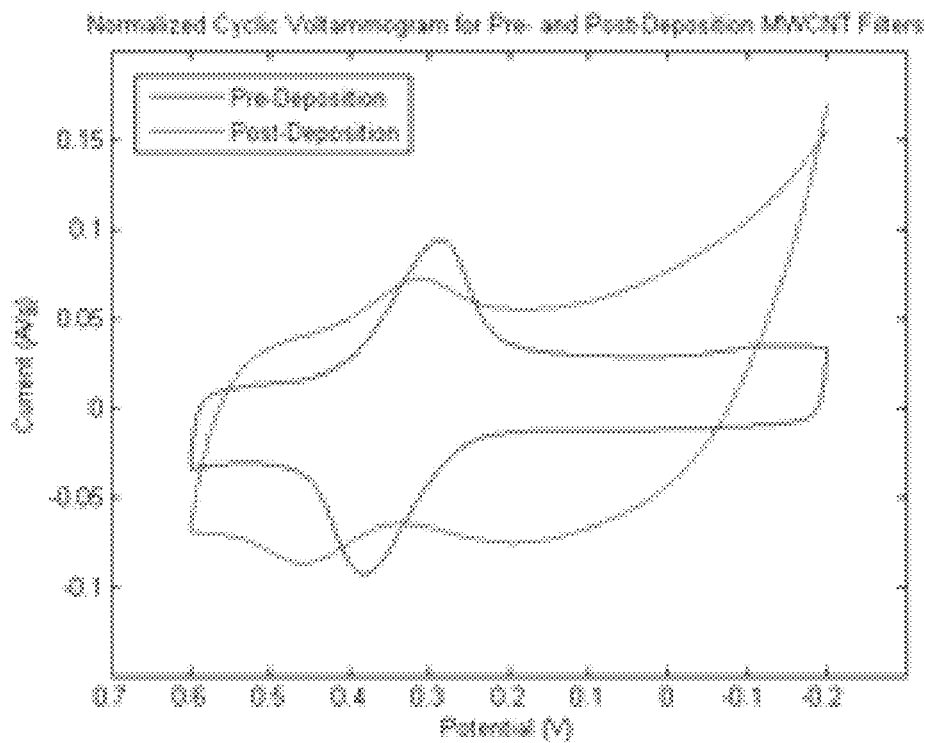
FIG. 9 is a graph that illustrates characterization of a pre-deposition flow-through sensor and a post-deposition flow-through sensor.

Due to the three-dimensional geometry of the CNT-MM filters, the CV data may be normalized by flow-through sensor mass in order to account for variation in growth. FIG. 9 is a graph that illustrates characterization of a pre-deposition flow-through sensor and a post-deposition flow-through sensor. FIG. 9 illustrates that a pre-deposition flow-through sensor is more electrochemically active with respect to a mediator solution than a post-deposition flow-through sensor. For this reason, all CV data was normalized according to flow-through sensor mass. Hence, EASA calculations can be used to determine the active specific surface area (SSA; EASA per unit mass) for each flow-through sensor so as to account for dimensional variation between flow-through sensors.

In some implementations, a non-coated flow-through sensor can have an active SSA of 271.33 $cm^2/g$ when tested within the ferricyanide mediator solution, indicating that the CNT-MM-based flow-through sensor is desirable for electrochemical applications. ~30 wt % Pt-CNT-MM flow-through sensor can be fabricated under two different $O_2$ etching schemes and can have an average active SSA of 57.38 $cm^2/g$ with a standard deviation of only 5.93 $cm^2/g$, suggesting that $O_2$ etching has little effect on subsequent Pt coverage within the etching duration studied (0-7 min with $O_2$ flowing). The near five-fold reduction in active SSA between the non-coated and Pt-coated flow-through sensors can be related to the Pt coverage.

Figure 10:
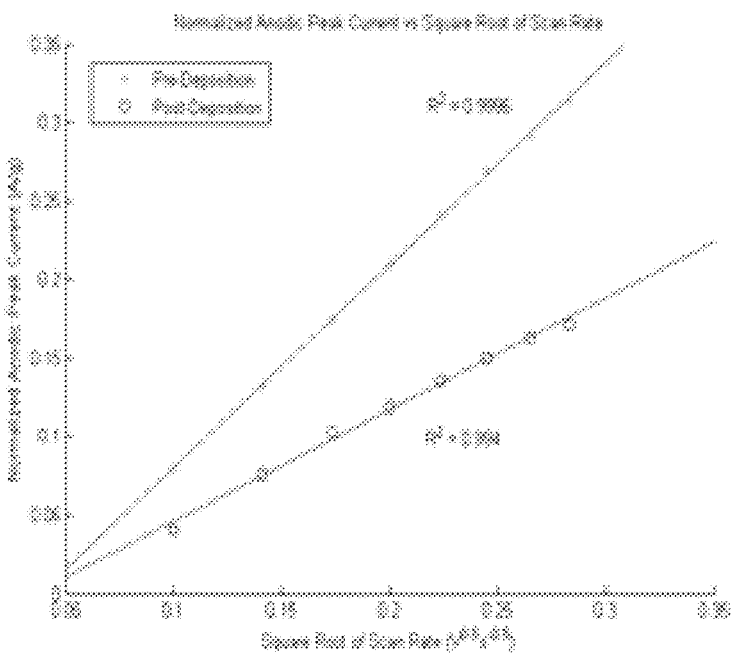
FIG. 10 illustrates a plot of a magnitude of a normalized anodic peak current versus the square root of the scan rate for both a pre- and post-deposition CNT-MM flow-through sensor.

FIG. 10 illustrates a plot of a magnitude of a normalized anodic peak current versus the square root of the scan rate for both a pre- and post-deposition CNT-MM flow-through sensor. As shown in FIG. 10, a linear relationship between the magnitude of the normalized anodic peak current and the square root of the scan rate for both a pre- and post-deposition CNT-MM flow-through sensor within the ferricyanide mediator solution can exist. This linear correlation, for which $R^2$ values of greater than 0.99 were achieved, suggests that the redox reaction of ferricyanide at the Pt surface may be a diffusion-controlled process.

In some implementations, non-coated CNT-MM flow-through sensors can exhibit a type II nitrogen adsorption isotherm indicative of a macroporous material, with a calculated Brunauer-Emmett-Teller surface area of 61 $m^2/g$ and a pore volume of 0.118 $cm^3/g$. Following the same trend as was found in the CV data, loading the CNT-MM flow-through sensors with Pt (~30 wt %) can result in a notable decrease in surface area (14 $m^2/g$) and pore volume (0.0281 $cm^3/g$). In some implementations, this decrease in BET surface area may be attributable to the increased density of the structure after catalyst deposition. In some implementations, pore size contributions for materials can be relatively wide and may not exhibit distinct peaks.

In some implementations, an increase in reactant concentration, catalytic surface area, and flowrate can, alone, or in various combinations, contribute to flowrate through a flow-through sensor.

As noted above, in some implementations, CNT-templated microfabrication techniques can be used to fabricate carbon-infiltrated multi-walled CNT scaffolds composed of highly ordered and aligned microchannels with desired geometry. Furthermore, urchin-like Pt nanoparticles can then be deposited onto, and throughout, the entirety of the CNT-MMs to provide a high aspect ratio catalytic microstructure for the enhanced propulsion of MUVs. In some implementations, Pt nanoparticle can be deposited onto carbon-infiltrated CNT-MMs. In some implementations, a flow-through sensor (e.g., the flow-through sensor 100 shown in FIG. 1) can be produced using the union between CNT-templated microfabrication and chemical deposition of nanoparticles. Such an electroless deposition technique is capable of depositing nanoparticles~200 μm deep within the pores of the CNT microchannels.

In some implementations, post $O_2$ etched CNT-MM and Pt-CNT-MM flow-through sensors can demonstrate hydrophilic behavior, which can be suited for aqueous-based characterization and propulsion methods and can be a significant shift from the hydrophobic nature of non-etched CNT-MMs. In some implementations, CNT-MM flow-through sensors can achieve an average electroactive surface area of, for example, 293±28 $cm^2$ $g^{-1}$ (in some implementations, greater or lesser values can also be achieved) within a ferricyanide based CV solution. Additionally, effective activation energy testing of Pt-CNT-MM flow-through sensors revealed a favorable performance of, for example, 26.96 kJ $mol^{-1}$ (in some implementations, greater or lesser values can also be achieved).

In some implementations, Pt-CNT-MMs as flow-through sensors can be functionalized in 25-30% w/w Pt—C solution. As discussed above, a flow-through sensor can be formed using CNT-MM Fabrication. In some implementations, a silicon wafer can be coated with a relatively thin aluminum oxide film ($Al_2O_3$, >30 nm) using e-beam evaporation primarily to act as a barrier to subsequent reactions between the iron layer and the underlying silicon substrate. In some implementations, AZ nLOF2020 photoresist can be applied (e.g., can be spun on at 2750 rpm for 60 seconds) and soft baked (e.g., soft baked at 110° C. for 60 seconds). In some implementations, CNT-MM pore geometry and dimensions (diamond shape with nominal diagonal dimensions (e.g., dimensions of 4.5×9.0 µm) can be defined on the wafer by photolithography, and hard baked (e.g., hard baked at 110° C. for 60 seconds). In some implementations, the photoresist can be developed (e.g., developed in a lightly agitated, AZ300MIF solution). In some implementations, a relatively thin iron film (Fe, ~7 nm) can be thermally evaporated onto the wafer surface as a catalyst for CNT growth. In some implementations, the wafer can be sonicated in solvent (e.g., insolvent for >10 minutes), rinsed (e.g., with Isopropyl Alcohol (IPA)), and dried (e.g., with compressed air to remove the entire photoresist layer and portions of the Fe layer in a lift-off process). In some implementations, to protect the wafer during flow-through sensor dicing, a relatively thin photoresist layer (e.g., AZ 3330) can be applied to (e.g., can be spun on) the wafer and soft baked. In some implementations, flow-through sensors can be diced into (e.g., diced into 16.93×16.93 mm) squares or other shapes using a dicing saw. In some implementations, preparatory to CNT growth, diced flow-through sensors with patterned Fe can be solvent cleaned to remove the protective photoresist layer.

In some implementations, CNT-MMA flow-through sensors can be grown, released, and/or cleaned. After a quality inspection check with an optical microscope, diced flow-through sensors can be placed on a quartz boat (e.g., in a Lindberg/Blue M Tube Furnace) for CNT growth. In some in some implementations, CNTs can be grown (e.g., for 26 minutes in flowing hydrogen ($H_2$, ~216 sccm) and ethylene ($C_2H_4$, 280 sccm) at 750° C.). In some implementations, this can result in a relatively substantial height of the CNT-MM (e.g., height of approximately 600 µm). In some implementations, CNT-MMs can then be coated with carbon in a subsequent infiltration step (e.g., at 900° C. for 20 minutes) with similar gases and flowrates as those used during CNT growth ($H_2$ at ~200 sccm and $C_2H_4$ at ~280 sccm). In some implementations, this can result in carbon-infiltrated CNTs with diameters of a lesser measurement than the height (e.g., approximately 290 nm). In some implementations, during carbon infiltration, the CNT-MM structure can self-release from the wafer substrate. In some implementations, CNT-MMs can be exposed to a brief (e.g., 7 minute $O_2$) plasma etching (e.g., at 300 W using an Anelva Reactive Ion Etcher (ME), DEM-451) to remove the carbon floor (additional carbon blocking the base of the CNT-MM channels) and enhance hydrophilicity to improve subsequent deposition of Pt catalyst (e.g., 5 minutes for removal of the carbon floor layer; 2 minutes for opposite face).

In some implementations, urchin-like Pt nanoparticle can be deposited within a flow-through sensor (e.g., flow-through sensor 100 shown in FIG. 1). Deposition of Pt onto a CNT-MM flow-through sensor can be performed on a per-mass basis to maintain, for example, a 25-30% w/w Pt—C solution loading. In some implementations, for a CNT-MM with a mass of, for example, 0.1071 g, 122.8 mg chloroplatinic acid hexahydrate can be weighed out (37.5% Pt, Sigma Aldrich 206083) and mixed with, for example, 2.0 mL formic acid (88% HCOOH, Macron 2592-05) and 18.0 mL ultrapure $H_2O$. These chemicals can be added to a beaker (e.g., 50 mL glass beaker (VWR, 89000-198)) whereupon their pH levels can be measured. In some implementations, the pH for this deposition can be acidic (e.g., 1.16), enabling urchin-like nanoparticle growth. In some implementations, using a slotted ring (e.g., a Teflon ring) for a flow-through sensor stand, the CNT-MM can be positioned vertically in a plating solution. In some implementations, keeping the flow-through sensor oriented in this manner can ensure that the Pt nanoparticles may nucleate and grow on the carbon substrate rather than precipitating out of solution and simply collecting on the flow-through sensor face. As a specific example of an implementation, a mass of a CNT-MM that is 0.1071 g, the solution molarity (11.80 mM) can correspond to a 30.07% w/w Pt—C loading. In some implementations, the beaker can be covered by material until the deposition process is completed, as indicated by a solution color change from amber to clear. Upon removal from the beaker, and prior to subsequent testing, a flow-through sensor can be submerged in deionized water (e.g., for at least 5 minutes) and then placed in a dehydration bake (e.g., an Ultra-Clean 100 (3497M-3) dehydration bake oven for a minimum of 8 minutes).

In some implementations, electrodes can be attached for cyclic voltammetry testing of a flow-through sensor. In some implementations, a silver epoxy can be used to attach Nichrome wire to each flow-through sensor used for CV testing. After the silver epoxy is cured (e.g., approximately 24 hrs), a chemically inert lacquer coating can be applied to the silver joint. In some implementations, CV tests can be conducted using a three-electrode cell with the CNT-MM flow-through sensors acting as the working electrode, a Ag/AgCl electrode acting as the reference electrode and a coiled Pt wire as the counter electrode. In some implementations, tests can be performed using a ferricyanide solution acting as mediator. In some implementations, multiple cycles (e.g., 3 cycles, 5 cycles, 10 cycles, 100 cycles) can be run per flow-through sensor test through a potential range (e.g., of −0.2-0.6 V) at a scan rate (e.g., of 10 mV s$^{-1}$). In some implementations, the peak redox current for each flow-through sensor can be taken as the average of both anodic/cathodic peak currents of the latter two CV cycles. In some implementations, runs can be performed at room temperature.

In some implementations, nitrogen gas adsorption testing of a flow-through sensor can be performed. In some implementations, Nitrogen adsorption analysis can be performed at a temperature such as 77 K. In some implementations, portion of the sensors can be degassed (e.g., at 100° C.) prior to analysis. In some implementations, surface area can be calculated by the Brunauer-Emmett-Telller (BET) method, pore size can be measured by the Barrett-Joyner-Halenda (BJH) method using the adsorption branch of the isotherm, and total pore volume can be determined by the single point method at relative pressure (P/P0) 0.97.

In some implementations, effective activation energy tests, by $H_2O_2$ decomposition, can be conducted using Pt-CNT-MM flow-through sensors fabricated following one or more of the procedures described above. Each flow-through sensor can be tested two or more times, after which the pressure data can be averaged per flow-through sensor. The test apparatus can include flasks (e.g., two, 125 mL, round-bottom flasks). In some implementations, one flask can be used for the Pt-CNT-MM test environment and the other as a reference environment. In some implementations, magnetic stir bars can be placed inside each flask and rotated (e.g., at 250 rpm) to increase the amount of $H_2O_2$ contacting the catalytic Pt-CNT-MM flow-through sensors and mimic, in part, the convective flow environment experienced through injection of $H_2O_2$ fuel into a MUV. In some implementations, to ensure the flasks are airtight, rubber septums with a rim seal can be positioned on each flask. In some implementations, the flasks can be placed inside ice or water baths on top of a hot plate stirrer to maintain isothermal conditions during each of the two or more runs per flow-through sensor (0° C., 17.5° C. and 35° C.). In some implementations, to ensure that steam may not be produced during testing, such that all generated pressure can be due to the release of $O_2$, a relatively low concentration $H_2O_2$ solution (1% w/w $H_2O_2$, diluted from 30% w/w $H_2O_2$) can be used for all tests. In some implementations, the $H_2O_2$ solution stock can be placed within a container (e.g., a 50 mL container) and immersed in the respective ice/water baths in order to achieve thermal equilibrium prior to testing. After achieving thermal equilibrium, each flask can be vented by temporary insertion of an unattached needle and allowed to equilibrate with atmospheric pressure. In some implementations, the amount of $O_2$ generated during each test can be measured as a pressure differential between the testing and reference environments. In some implementations, to measure the pressure differential, n differential pressure manometer (e.g., measuring up to ±5 psi/34.5 kPa) can be connected to each flask via two high strength silicone tubes (e.g., diameter 0.375 in/9.525 mm). In some implementations, the tubing can be connected to the manometer and syringe needles using barbed fittings. In some implementations, the two syringe needles connected to the pressure manometer can be inserted into the test and control flasks, respectively, by piercing through the diaphragm of each septa. In some implementations, the differential pressure between the test and control flasks can be zeroed before recording data and then measured as a function of time with a computer via a connection (e.g., a universal serial bus (USB) connection). In some implementations, $H_2O_2$ solution (e.g., 10 mL of the $H_2O_2$ solution) can be simultaneously injected into each flask while a stir bar (e.g., the magnetic stir bars) stirred the solution (e.g., at 200 rpm). In some implementations, resultant differential pressure vs. time data can be used to determine catalyst performance and effective activation energy with the Arrhenius Equation.

Figure 11:
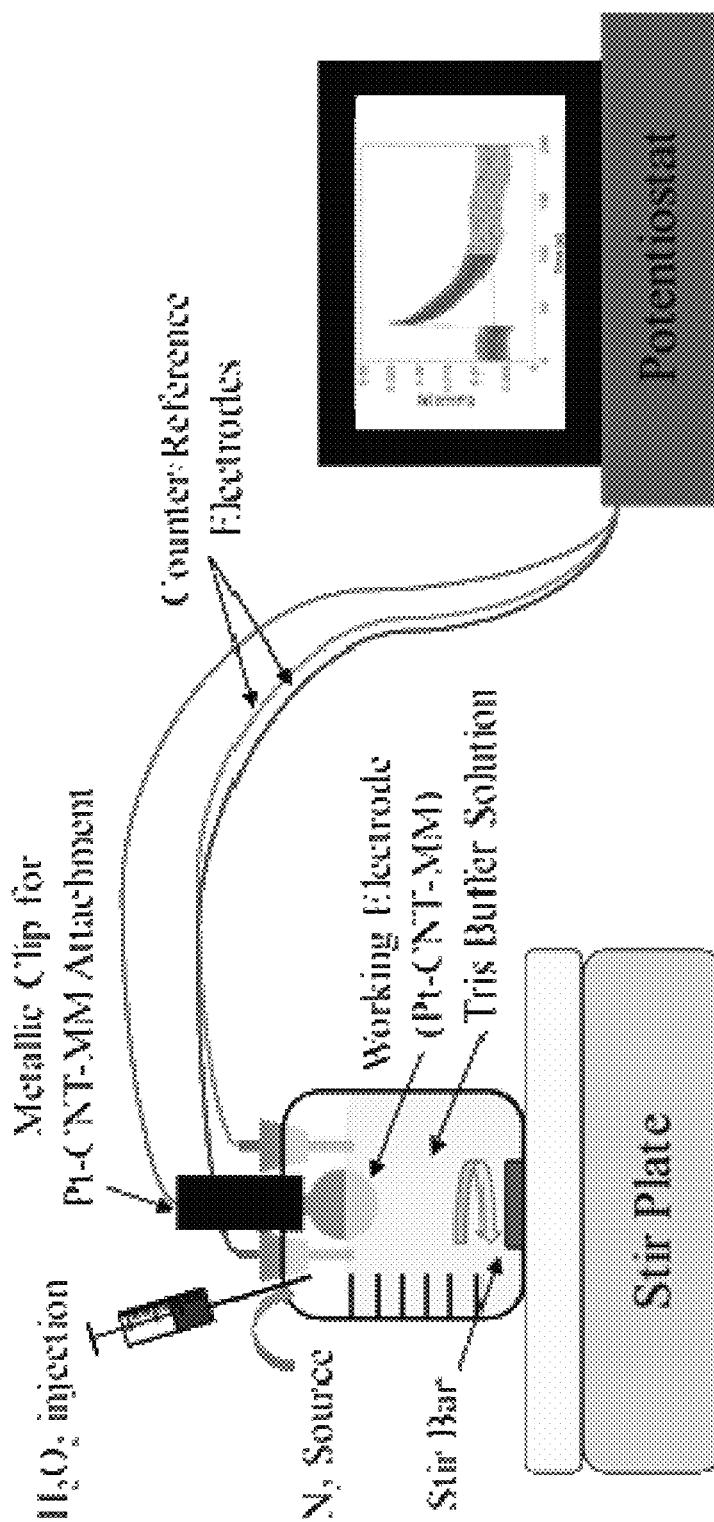
FIG. 11 illustrates a three electrode cell that can be used for chronoamperometric testing of Pt-CNT-MM flow-through sensors in static and stirred environments of $H_2O_2$.

FIG. 11 illustrates a three electrode cell that can be used for chronoamperometric testing of Pt-CNT-MM flow-through sensors in static and stirred environments of $H_2O_2$. Flow-through sensors can be positioned such that approximately half of the flow-through sensors are submerged in solution. Convective enhancement of an analyte flow field can drastically effect the molar oxidation rate at a sensing surface of a flow-through sensor. Accordingly, the measured current per given analyte concentration (sensitivity) is enhanced. To demonstrate this point, and to establish a baseline against which to compare through-flow sensing, chronoamperometric testing of Pt-CNT-MMs can be conducted in static and stirred environments of $H_2O_2$.

Pt-CNT-MM flow-through sensors can be fabricated according to the methods described herein and can be functionalized by an electroless Pt deposition process (~30% w/w Pt—C). Chronoamperometric testing can be performed in a three electrode cell with a flexible Ag/AgCl reference electrode (saturated KCl), Pt wire counter electrode, and the Pt-CNT-MM structures operating as the working electrode with an applied voltage of 700 mV in a Tris buffer solution (25 mM Tris, $(HOCH_2)_3CNH_2$; 0.5 M NaCl; pH 10.0). It is here noted that this same Tris buffer composition can be used during testing. An $N_2$ envelope can be maintained above the buffer solution in order to prevent interference from the diffusion of oxygen into the electrochemical cell. Aliquots of $H_2O_2$ can be prepared (e.g., prepared from 0.800±0.002 M stock $H_2O_2$ solution).

Figure 12:
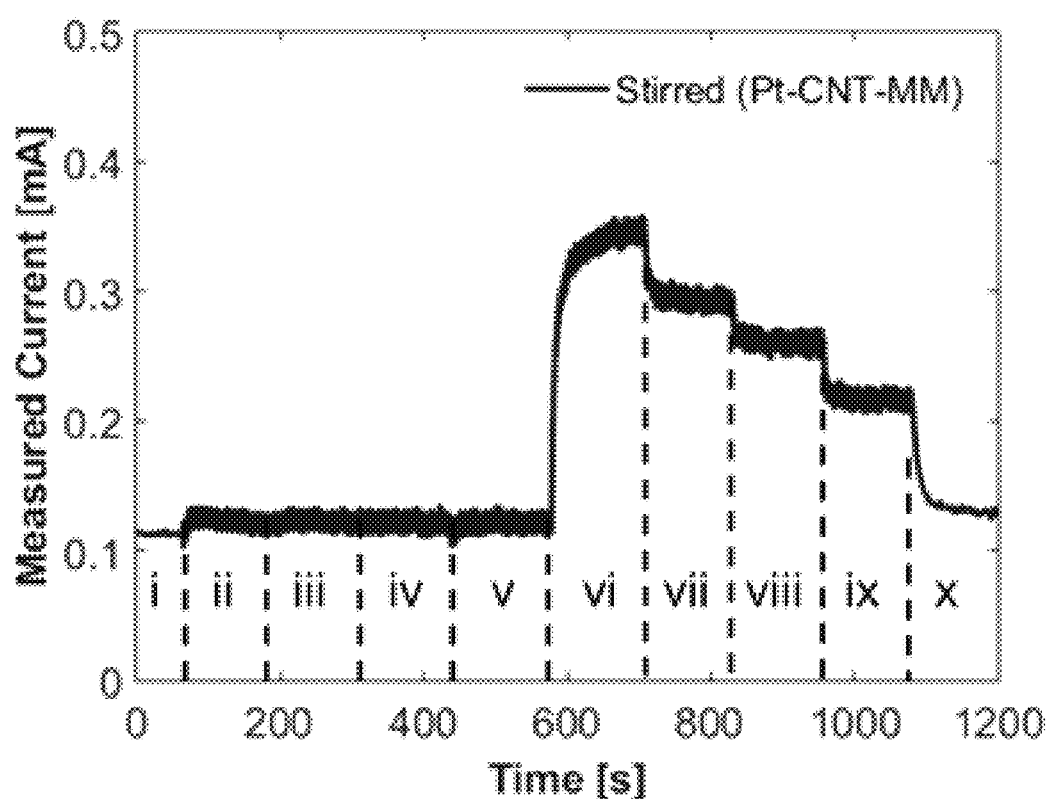
FIG. 12 is a graph that illustrates measured current versus time related to a Pt-CNT-MM.

Upon applying an electric potential, reduction of the stirred buffer solution (and dissolved oxygen in solution) can produce a large measurable current. As the reduction process continues, the current can eventually reach a reference baseline from which an absolute $H_2O_2$ oxidation current can be measured. Reference baselines for the reduced buffer solution can be measured for static and stirred cases, each case lasting about 2 min (50, 75, 100, and 150 rpm). It can be observed that the buffer baseline does not change significantly with increasing stir speed. After sufficiently reducing the stirred buffer solution, and once the solution has maintained a stir speed of 150 rpm for approximately 2 min, 5 μL of stock $H_2O_2$ (0.800 M) can be injected into the 35 mL buffer solution achieving a 114 μM solution, similar to a realistic concentration of glucose in saliva. Electrical current measurements can be taken throughout the test, with the stir speed decreased at the beginning of each 2 min interval. The results are illustrated in FIG. 12.

Figure 13:
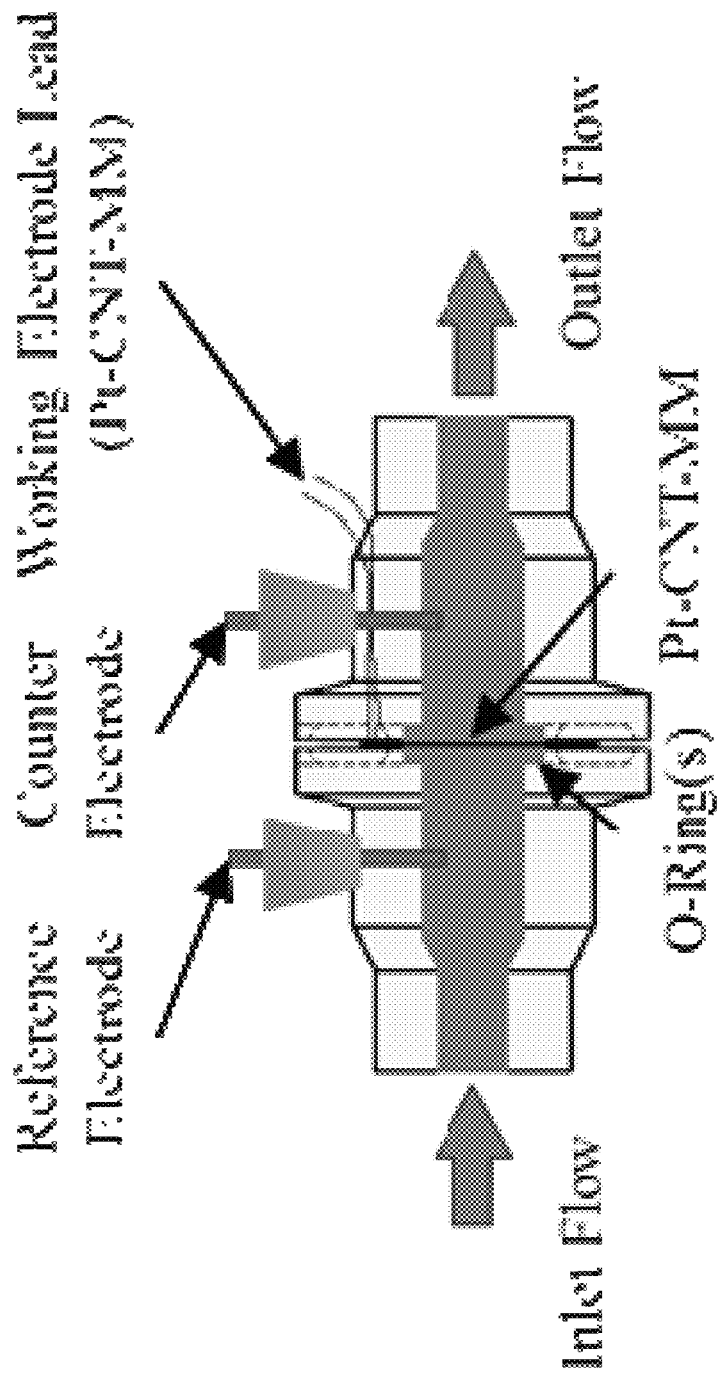
FIG. 13 illustrates a Teflon flow cell configuration for through-flow chronoamperometric testing.

In some implementations, the coupled transport enhancement made possible by an increase in surface area and analyte flow can be further enhanced by boundary-layer confinement. Accordingly, the utility of Pt-CNT-MMs applied in a through-flow environment can be demonstrated and can dramatically increase chemical analyte introduction rates and thereby improve upon conventional sensing methods. FIG. 13 illustrates teflon flow cell configuration for through-flow chronoamperometric testing of Pt-CNT-MM flow-through sensors for the investigation of mass transport enhancement via boundary layer confinement.

A suitable testing setup can be used in sensing of $H_2O_2$ in a through-flow environment. Specifically, a chemically inert flow cell can be used to allow for the inflow and outflow of dilute $H_2O_2$ in a buffer solution. The flow cell can secure a water-tight seal across Pt-CNT-MM flow-through sensors without causing damage to the flow-through sensors. Finally, the flow cell can allow for electrode access into the chemical flow, thereby forming a dynamic electrochemical cell. The Teflon flow cell shown in FIG. 13 can be used for through-flow chronoamperometric testing of Pt-CNT-MM flow-through sensors.

Flow-through sensors can be secured within the flow cell, which can be connected to a syringe pump. The feeder syringe, located on the syringe pump, can function to infuse and withdraw the Tris base buffer solution into, and out of, the flow cell. Air within the flow cell can be evacuated as buffer solution can be initially infused from the syringe pump. Exposed buffer solution can be collected in a reservoir syringe which can be exposed to a continuous stream of $N_2$ gas. Reduction of the buffer solution, in preparation for sensing of $H_2O_2$, involved repeatedly cycling the buffer solution through the flow cell while the 700 mV working potential was applied to the Pt-CNT-MM flow-through sensor. Once reduced, chronoamperometric testing can be performed.

Figure 14:
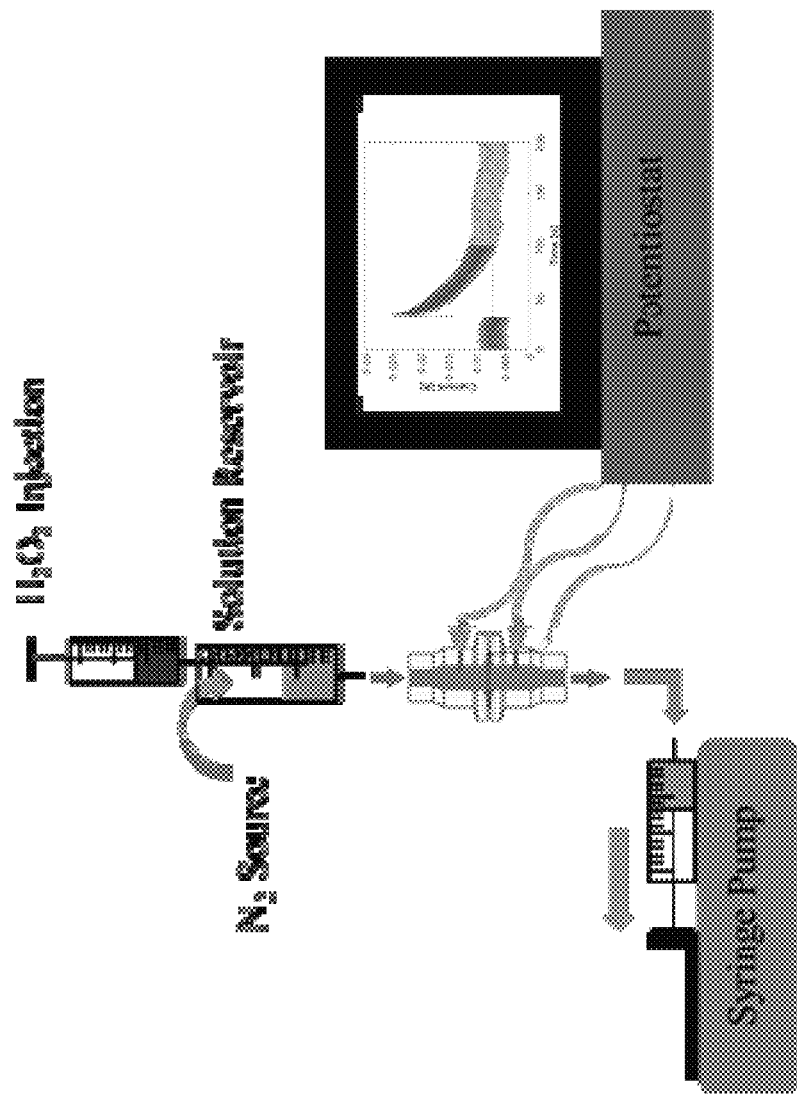
FIG. 14 is a diagram that illustrates a through-flow chronoamperometric setup using flow cell.

FIG. 14 is a diagram that illustrates a through-flow chronoamperometric setup using flow cell. Pt-CNT-MM flow-through sensors housed in flow cell act as the working electrode while the buffer solution with trace $H_2O_2$, is pumped through for sensing.

Figure 15:
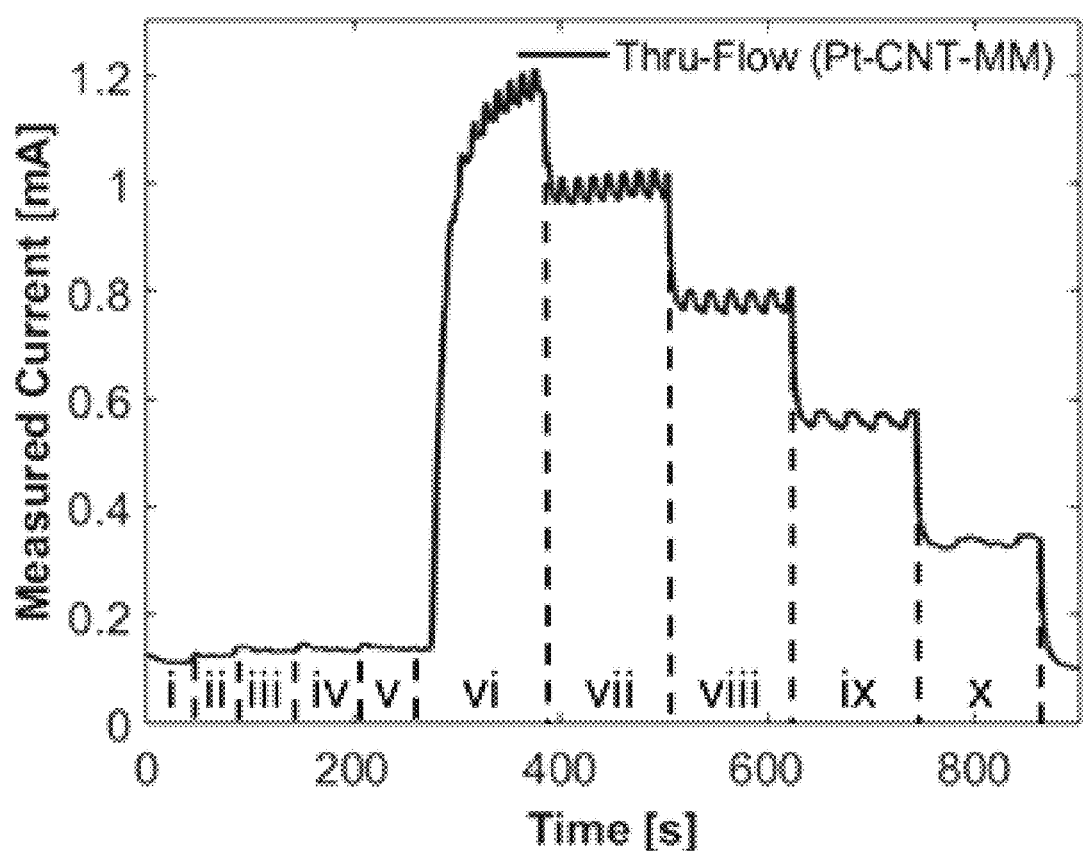
FIG. 15 illustrates an example chronoamperometric sensing.

FIG. 15 illustrates an example chronoamperometric sensing of 114 μM $H_2O_2$ (in Tris buffer) in through-flow setup using large circle patterned Pt-CNT-MM. Tris buffer reference baseline for through-flow environment at (i) 10, (ii) 20, (iii) 30, (iv) 40, and (v) 50 μL s$^{-1}$ (measured for ~1 min per interval). After injection of stock $H_2O_2$ solution (0.800 M), measured electrical currents were taken for through-flow environments at (vi) 50, (vii) 40, (viii) 30, (ix) 20, and (x)

10 µL s$^{-1}$. Note that there was some delay between the point of injection (beginning of vi) and rise in electrical current because of the time required for the injection to reach the Pt-CNT-MM flow-through sensor within the flow cell. Also, note that the signal frequency decreases with successive intervals from vi to x due to stepping of the syringe pump motor.

Through-flow chronoamperometric testing for Pt-CNT-MMs can be conducted in a stepwise fashion, similar to that of the static and stirred testing. Using a syringe pump, Tris buffer solution (of the same composition as was used for static/stirred testing) can be cycled through the Pt-CNT-MMs until fully reduced (see FIG. 14). The buffer solution can then withdrawn through the Pt-CNT-MMs and into the pump syringe while baseline electrical currents can be measured for 10, 20, 30, 40, and 50 µL s$^{-1}$ flowrates, respectively (see FIG. 15). Upon completion of measuring the baseline current for 50 µL s$^{-1}$, $H_2O_2$ can be injected into the $N_2$ bubbled Tris reservoir so as to create a $H_2O_2$ solution of approximately 114 µM within the reservoir (typically a 3.1 µL injection of 0.8 M $H_2O_2$ into 22 mL of Tris buffer). Upon entering the flow cell, the measured current can be observed to increase dramatically, and decrease with each successive decrease in flowrate (flowrate stepped from 50 to 10 µL s$^{-1}$ at 2 min intervals).

Figure 16:
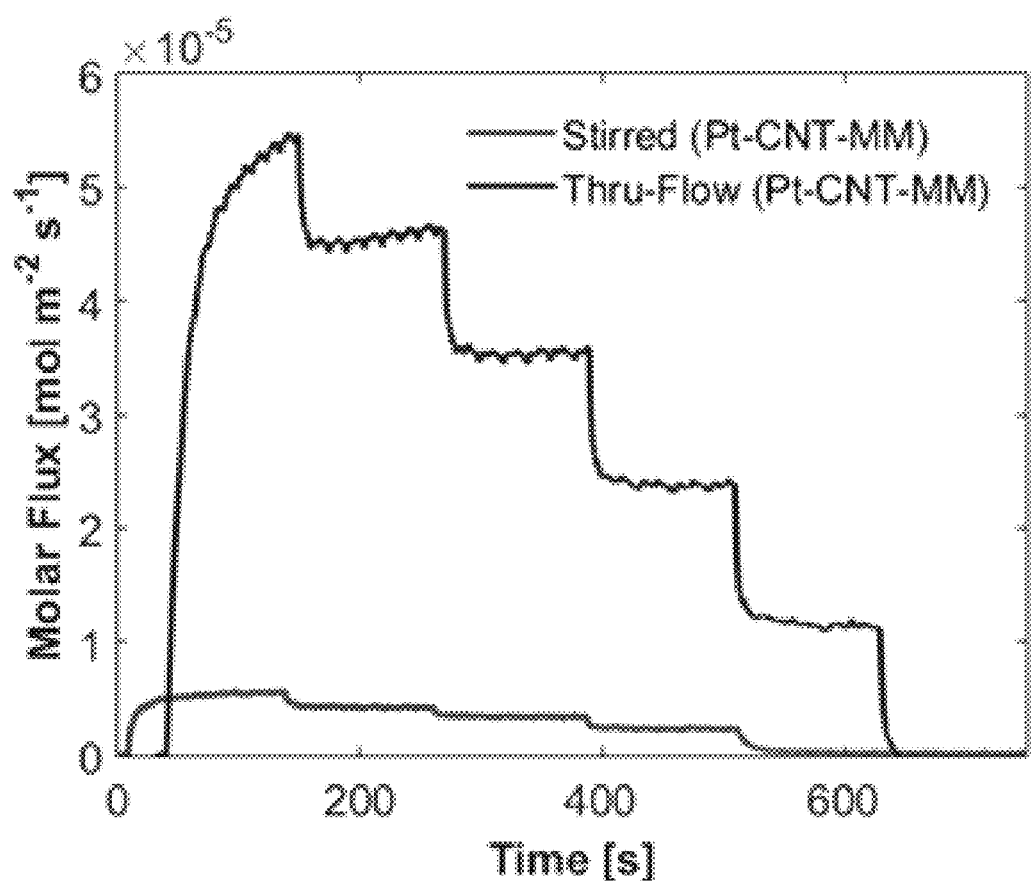
FIG. 16 illustrates chronoamperometric sensing using a Pt-CNT-MM flow-through sensor.

Initial testing can reveal much about the mass transport enhancement made possible by the Pt-CNT-MM microstructure in a through-flow environment, as well as its improvement on sensing performance compared to static/stirred conditions. Specifically, FIG. 16 illustrates a ten-fold increase in molar flux for the Pt-CNT-MM flow-through sensor between the initial stirred flow and through-flow conditions (150 rpm vs. 50 µL s$^{-1}$). Though a direct comparison of relative flowrates between stirred and through-flow conditions can be impractical, the large increase in molar flux can be attributed to both an increase in exposed electrocatalytic surface area, as well as increase in boundary layer confinement. It can be observed that, for the prescribed test conditions, the molar flux sensed using the Pt-CNT-MM structure in a through-flow environment at 10 µL s$^{-1}$ can be approximately twice that achieved by the Pt-CNT-MM flow-through sensor in a stirred environment at the maximum tested stir speed (150 rpm), and nearly fifty times that achieved in a static condition.

FIG. 16 illustrates chronoamperometric sensing of 114 µM $H_2O_2$ (in Tris buffer) using a Pt-CNT-MM flow-through sensor (same as used in FIG. 12). It should be noted that data for the Thru-Flow (Pt-CNT-MM) can have a buffer baseline that was slightly increasing prior (e.g., immediately prior) to $H_2O_2$ injection. Given that the data can be zeroed on the y-axis, and that the molar flux plateaus (shown above) can be fairly level, the sloping baseline likely contributes negligible error to the resultant plot.

Figure 17:
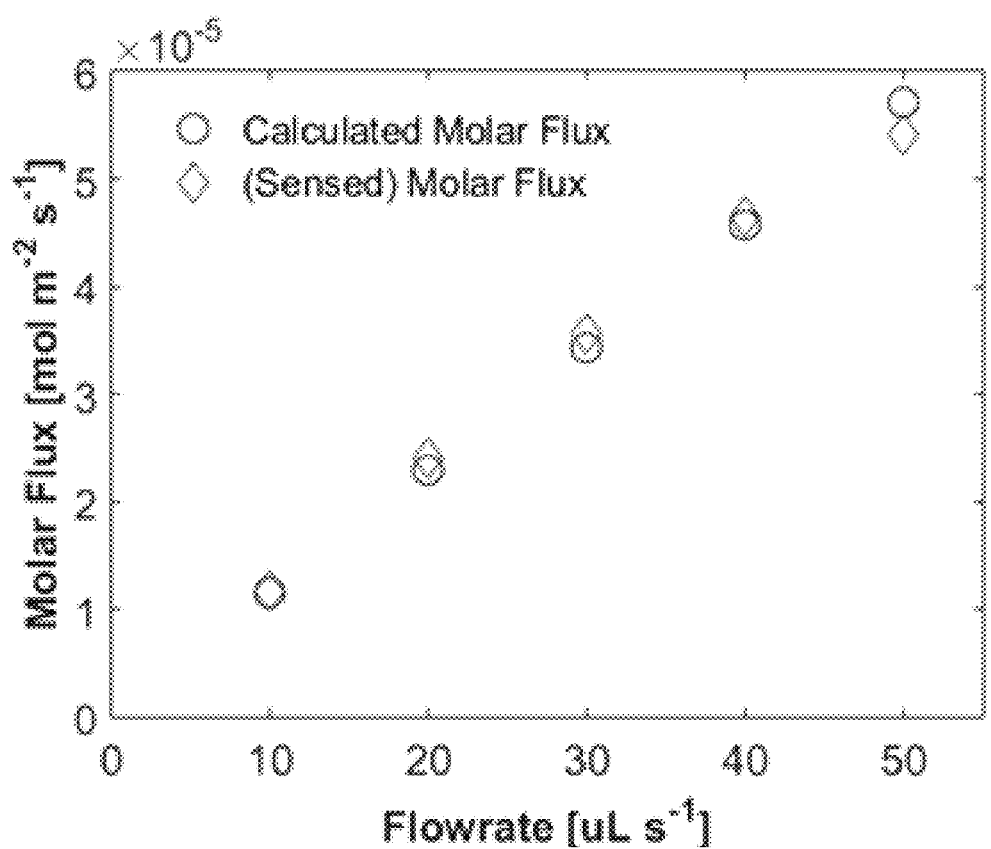
FIG. 17 illustrates a comparison of calculated versus sensed molar flux for a Pt-CNT-MM flow-through sensor.

Knowing both the $H_2O_2$ concentration of the buffer solution (114 µM) and the prescribed flowrate, the theoretical molar flux of the through-flow setup can be calculated and compared to the experimentally obtained molar flux sensed by a Pt-CNT-MM flow-through sensor (FIG. 17; plot based on data shown in FIG. 16). As shown in FIG. 17, the calculated molar supply rate can be nearly exactly matched by the sensed molar introduction rate, indicating that Pt-CNT-MM structures facilitate high mass transport from bulk solution to electrocatalytic surfaces for near-total oxidation of trace $H_2O_2$.

FIG. 17 illustrates a comparison of calculated versus sensed molar flux for a Pt-CNT-MM flow-through sensor in through-flow environment of 114 µM $H_2O_2$ in Tris buffer solution (calculated from data shown in FIG. 16). The plot illustrates relatively high mass transport from bulk solution to electrocatalytic surface of Pt-CNT-MM for near-total oxidation of suspended $H_2O_2$.

Some implementations may be implemented using various semiconductor processing and/or packaging techniques. Some embodiments may be implemented using various types of semiconductor processing techniques associated with semiconductor substrates including, but not limited to, for example, Silicon (Si), Galium Arsenide (GaAs), Silicon Carbide (SiC), and/or so forth.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments. It should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A flow-through sensor, comprising:
   a carbon nanotube structure including a parallel array of micro-channels;
   a catalyst coupled to an inner surface of at least one of the micro-channels; and
   a functionalizing material disposed within the micro-channels.

2. The flow-through sensor of claim 1, wherein the catalyst has a shape including an inner mass and protrusions protruding from the inner mass.

3. The flow-through sensor of claim 1, wherein the catalyst includes a platinum catalyst.

4. The flow-through sensor of claim 1, wherein the parallel array of micro-channels defines a close-packed diamond shape.

5. The flow-through sensor of claim 1, wherein a length:width aspect ratio of each of the micro-channels is greater than 40:1.

6. The flow-through sensor of claim 1, wherein a length:width aspect ratio of each of the micro-channels is greater than 100:1.

7. The flow-through sensor of claim 1, wherein the functionalizing material is a biorecognition material.

8. The flow-through sensor of claim 1, wherein the functionalizing material is coupled to the inner surface.

9. The flow-through sensor of claim 1, further comprising:
   a binding material, the functionalizing material being included in the binding material.

10. The flow-through sensor of claim 9, wherein the binding material is a conductive layer.

11. The flow-through sensor of claim 1, wherein a pore size of the each of the micro-channels from the parallel array of micro-channels is less than a micron.

12. The flow-through sensor of claim 1, wherein a pore size of the each of the micro-channels from the parallel array of micro-channels is greater or equal to a micron.

13. The flow-through sensor of claim 1, further comprising:

a detection mechanism configured to detect a current produced in response to an analyte reacting at the catalyst.

14. The flow-through sensor of claim 1, wherein the flow-through sensor is configured to detect an analyte concentration of less than or equal to 0.05 mM, or 0.05 mM to 50 mM.

15. A flow-through sensor, comprising:
a carbon nanotube structure including a parallel array of micro-channels, a catalyst, and a functionalizing material; and
a detection mechanism configured to detect a presence of a target material based on an electrical signal from the flow-through sensor produced from an interaction of the target material with the flow-through sensor.

16. The flow-through sensor of claim 15, wherein the interaction includes multiple reactions.

17. The flow-through sensor of claim 15, wherein the interaction at least two reactions.

18. The flow-through sensor of claim 15, wherein the interaction is a chemical reaction.

19. The flow-through sensor of claim 15, wherein the target material reacts with the functionalizing material in a first reaction, the first reaction results in a byproduct that reacts with the catalyst during a second reaction.

20. The flow-through sensor of claim 15, wherein the electrical signal is produced in response to electrons released during reaction of the target material with at least one of the catalyst or the functionalizing material.

\* \* \* \* \*